(12) United States Patent
Takei

(10) Patent No.: US 8,583,212 B2
(45) Date of Patent: Nov. 12, 2013

(54) MRI APPARATUS

(75) Inventor: Naoyuki Takei, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1228 days.

(21) Appl. No.: 12/392,225

(22) Filed: Feb. 25, 2009

(65) Prior Publication Data

US 2009/0221905 A1 Sep. 3, 2009

(30) Foreign Application Priority Data

Feb. 29, 2008 (JP) .................................. 2008-048923

(51) Int. Cl.
*A61B 5/05* (2006.01)

(52) U.S. Cl.
USPC ........................... 600/419; 324/307; 600/310

(58) Field of Classification Search
USPC ........................... 324/310; 600/410, 413, 419
See application file for complete search history.

(56) References Cited

U.S. PATENT DOCUMENTS

| | | | |
|---|---|---|---|
| 5,842,989 A * | 12/1998 | Zur | 600/410 |
| 7,030,609 B2 | 4/2006 | Pipe | |
| 7,205,763 B2 | 4/2007 | Porter | |
| 7,323,873 B2 | 1/2008 | Yamazaki | |
| 7,432,710 B2 | 10/2008 | Takei et al. | |
| 2002/0087067 A1* | 7/2002 | Foo | 600/413 |
| 2004/0092809 A1 | 5/2004 | DeCharms | |
| 2006/0224062 A1 | 10/2006 | Aggarwal et al. | |
| 2006/0264735 A1 | 11/2006 | Stemmer | |
| 2007/0088212 A1 | 4/2007 | Takei et al. | |
| 2007/0167733 A1* | 7/2007 | Miyoshi | 600/410 |
| 2008/0129289 A1 | 6/2008 | Stemmer et al. | |
| 2008/0169808 A1 | 7/2008 | Taniguchi et al. | |
| 2008/0180098 A1 | 7/2008 | Takei | |
| 2009/0005673 A1* | 1/2009 | Rehwald et al. | 600/420 |
| 2009/0270719 A1 | 10/2009 | Miyoshi | |
| 2010/0090693 A1 | 4/2010 | Wald et al. | |

OTHER PUBLICATIONS

Talagala et al., Whole-Brain 3D Perfusion MRI at 3.0 T Using CASL With a Separate Labeling Coil, Magnetic Resonance in Medicine 52:131-140 (2004).*

(Continued)

*Primary Examiner* — Long V. Le
*Assistant Examiner* — Ellsworth Weatherby
(74) *Attorney, Agent, or Firm* — Armstrong Teasdale LLP

(57) ABSTRACT

An MRI apparatus for imaging a subject so as to emphasize, more than a background tissue, a bodily fluid flowing through an imaging region of the subject, the apparatus includes a transmission coil for transmitting an RF pulse to the subject, a first transmission coil control device for controlling the transmission coil so that the transmission coil transmits a first inversion pulse for inverting longitudinal magnetization components of the bodily fluid and the background tissue to negative values from the positive values, a second transmission coil control device for controlling the transmission coil so that the transmission coil transmits a second inversion pulse for inverting the longitudinal magnetization component of the background tissue to the positive value from the negative value inverted by the first inversion pulse, a third transmission coil control device for controlling the transmission coil so that the transmission coil transmits a third inversion pulse for inverting the longitudinal magnetization component of the background tissue to the negative value from the positive value inverted by the second inversion pulse and a fourth transmission coil control device for controlling the transmission coil so that the transmission coil transmits an excitation pulse for acquiring data about the bodily fluid.

16 Claims, 22 Drawing Sheets

(56) References Cited

OTHER PUBLICATIONS

Simonetti et al., "Black Blood" T2-weighted Inversion Recovery MR Imaging of the Heart, Radiology 199: 49-57 (1996).*

Mitsue Miyazaki et al: Recent Development of Non-contrast-enhanced MR Angiography, Image Information Medical, Sangyo Kaihatsu Kiko Kabushiki Kaisha Sep. 2006, pp. 952-957.

Non-Final Office Action, U.S. Appl. No. 12/696,560 mailed May 7, 2012; 12 pages.

* cited by examiner

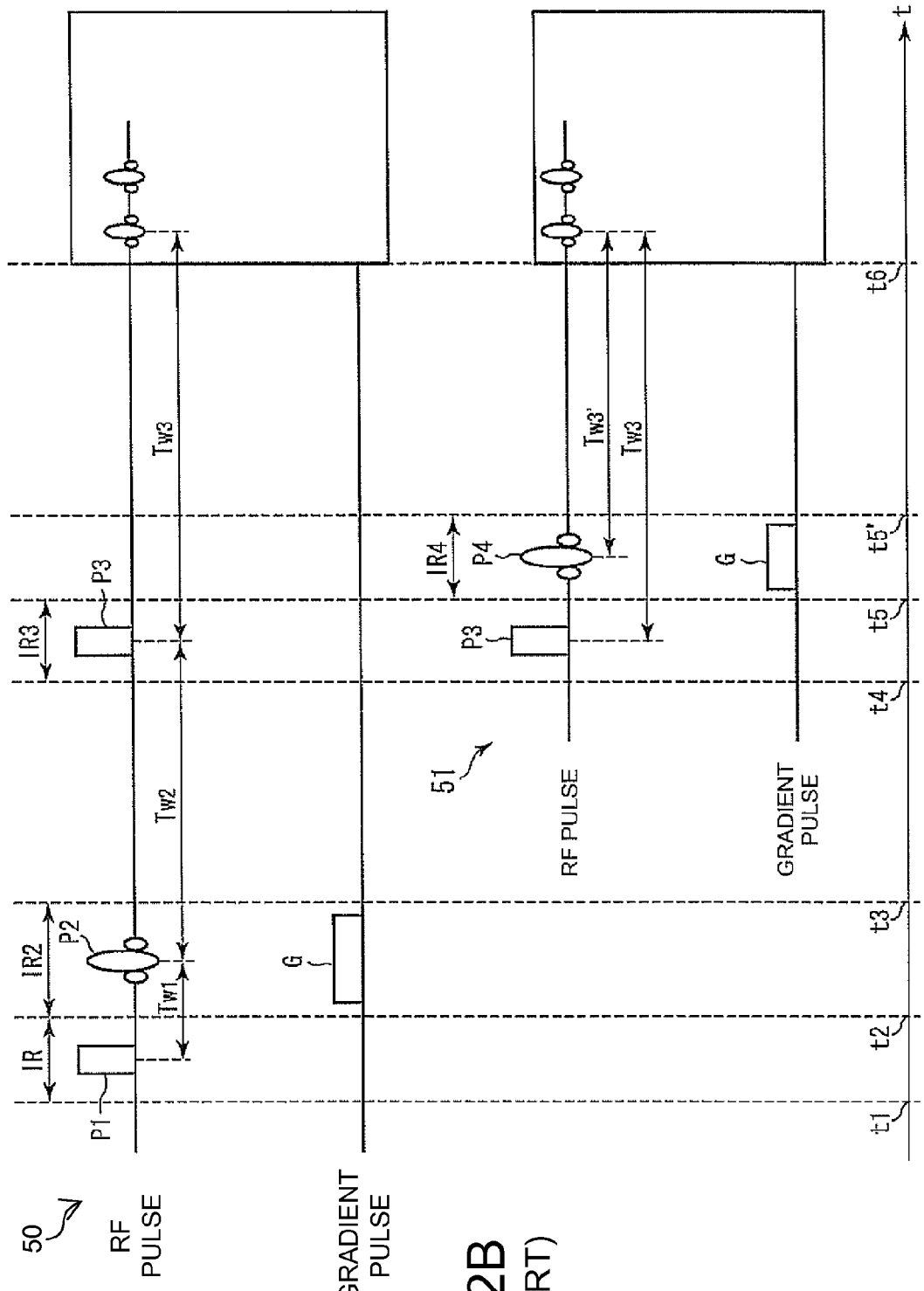

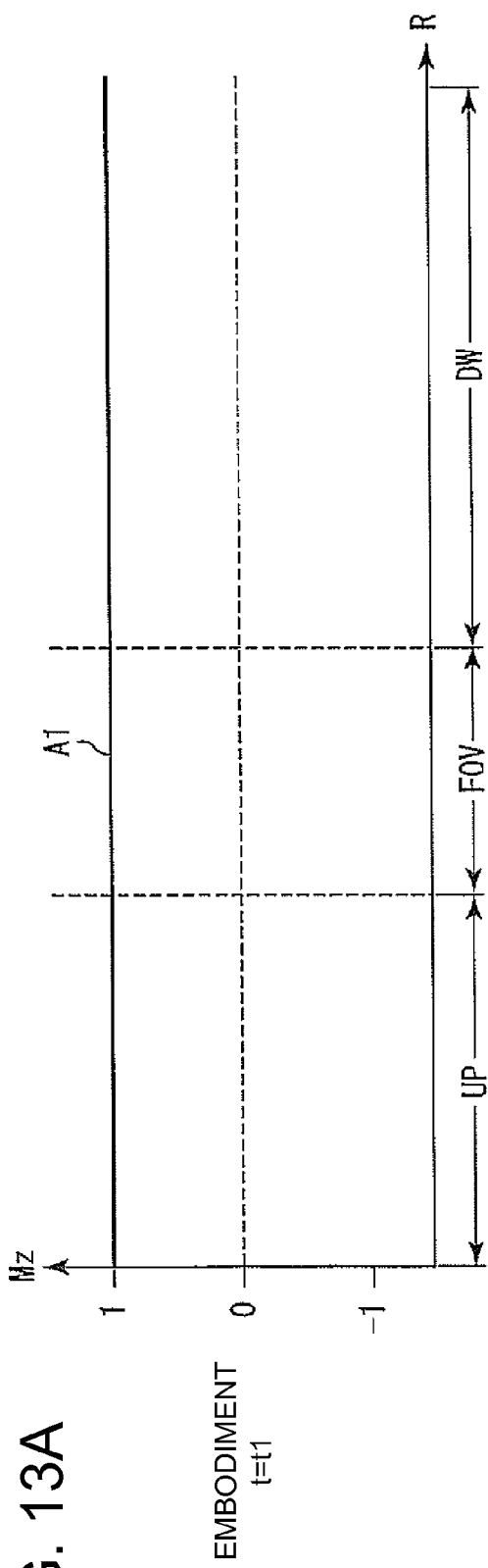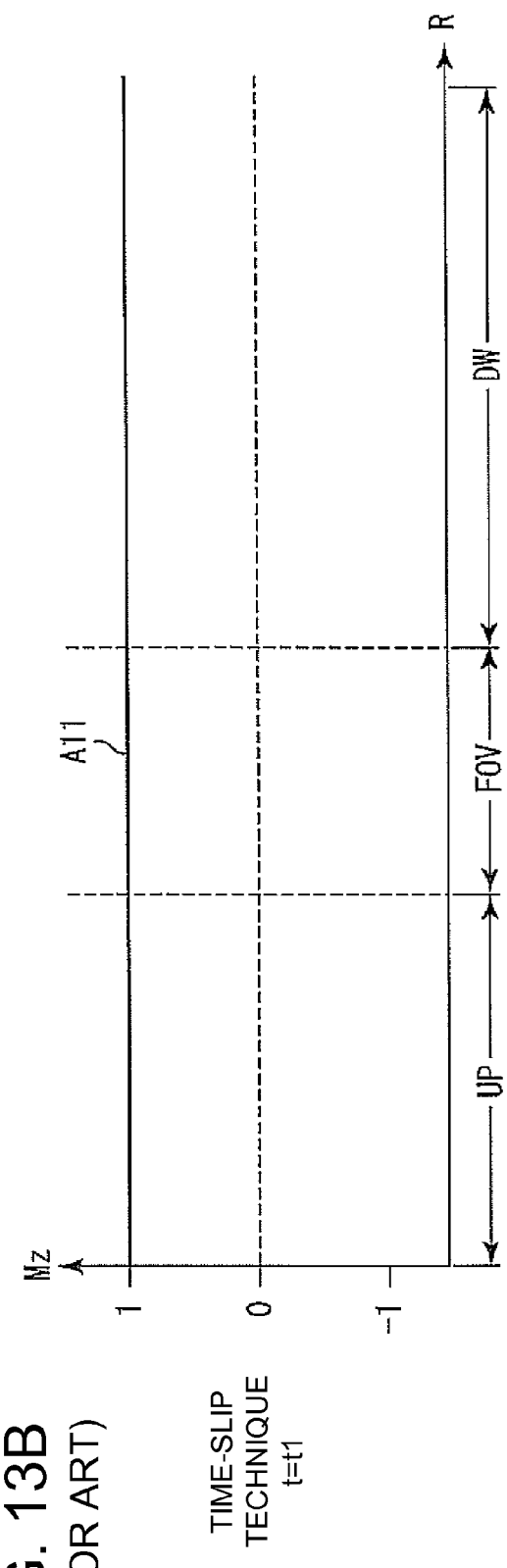

EMBODIMENT
t=t2

TIME-SLIP TECHNIQUE
t=t2

EMBODIMENT
t=t3

TIME-SLIP TECHNIQUE
t=t3

EMBODIMENT
t=t4

TIME-SLIP TECHNIQUE
t=t4

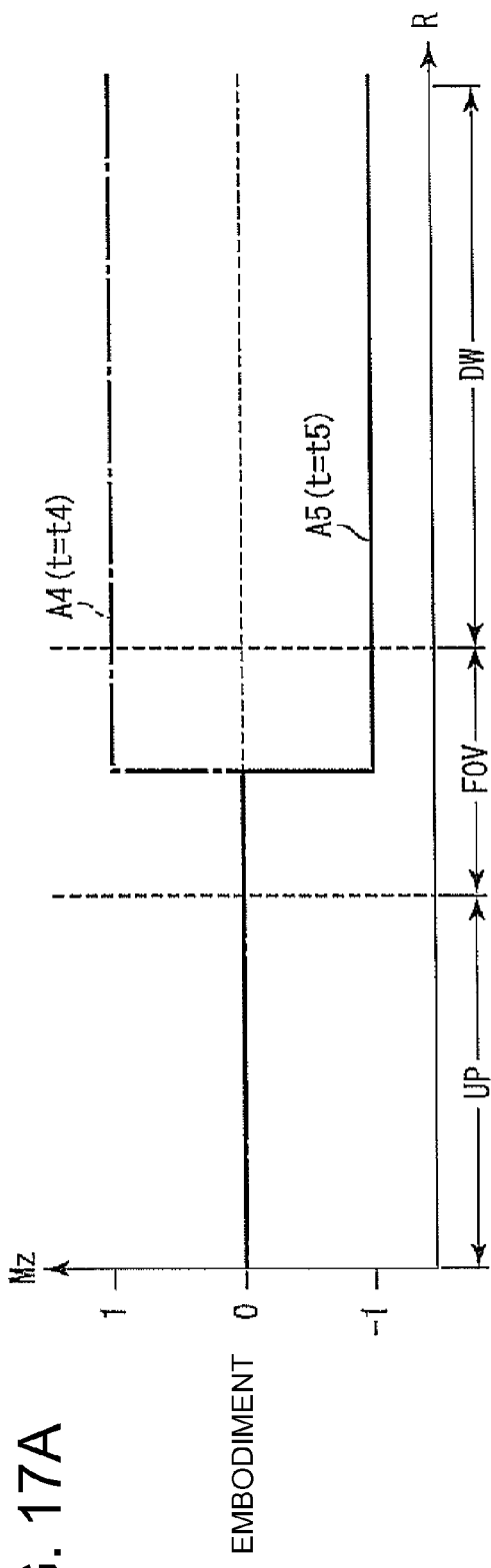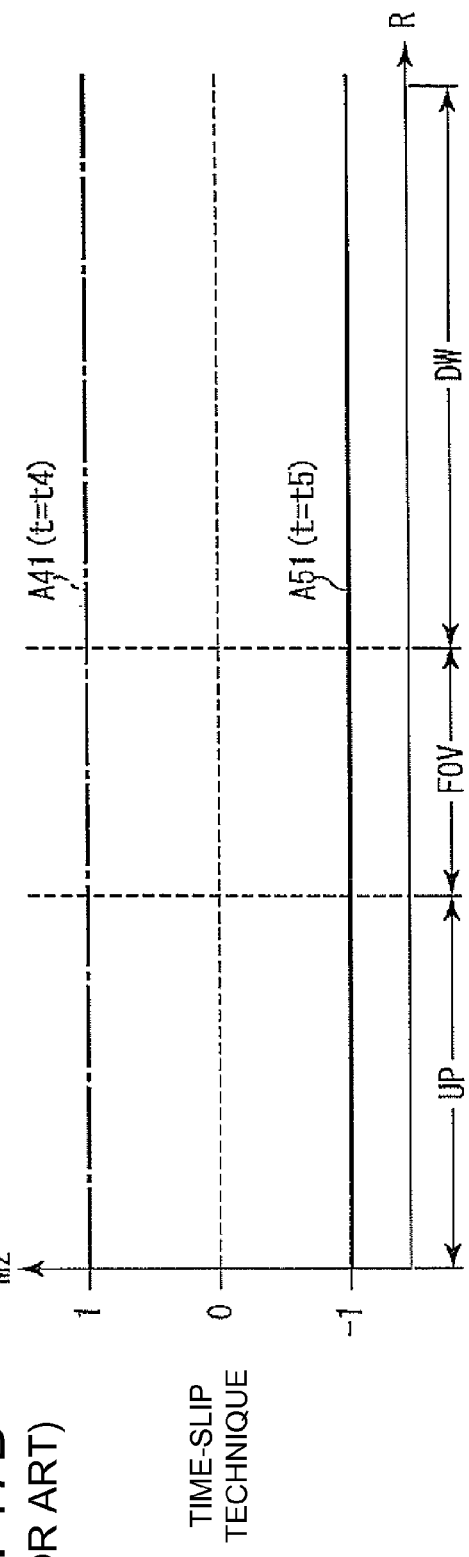

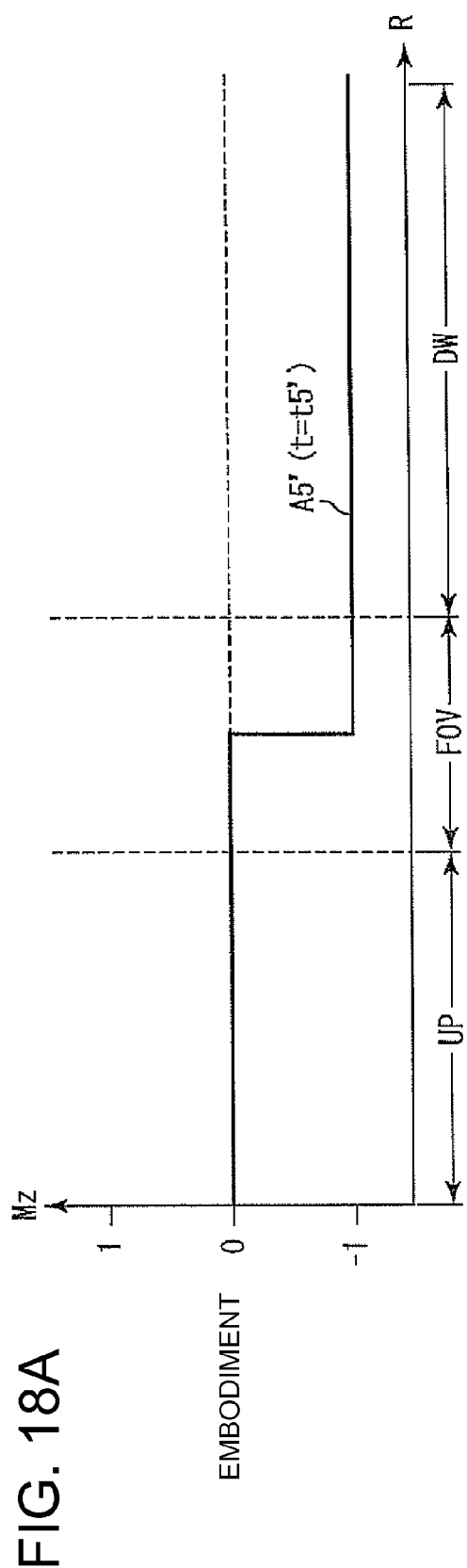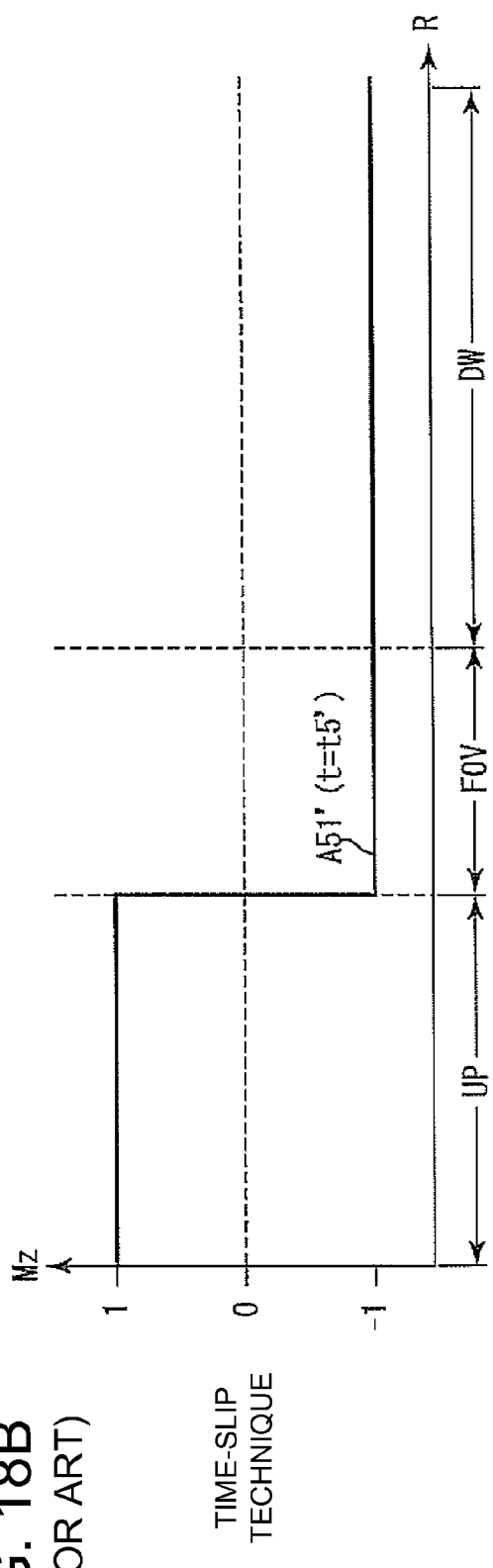

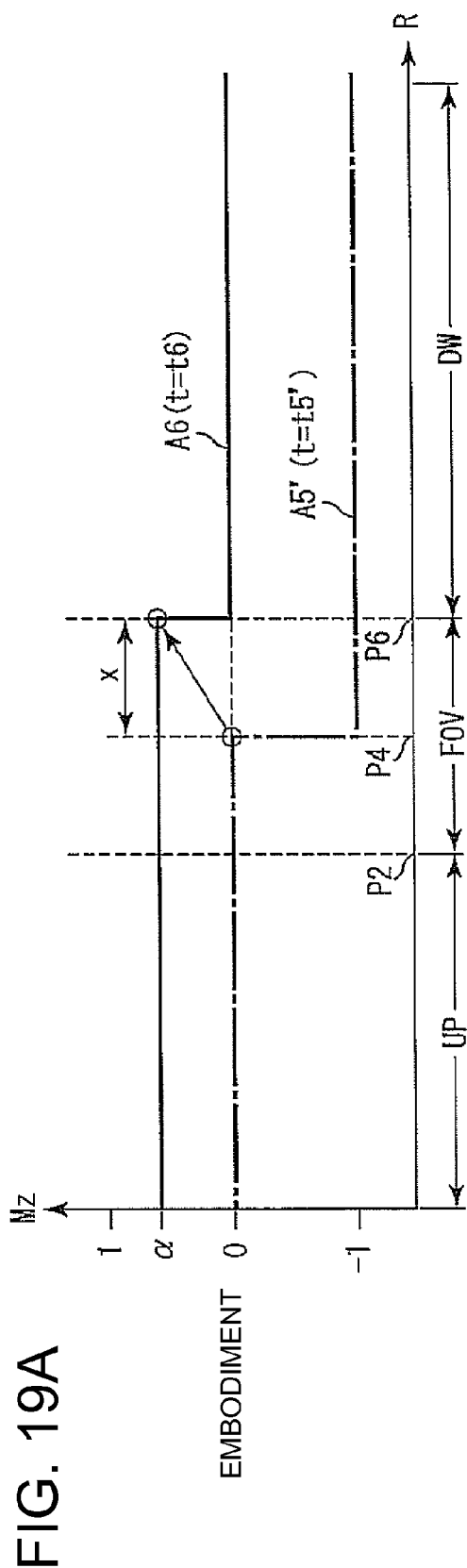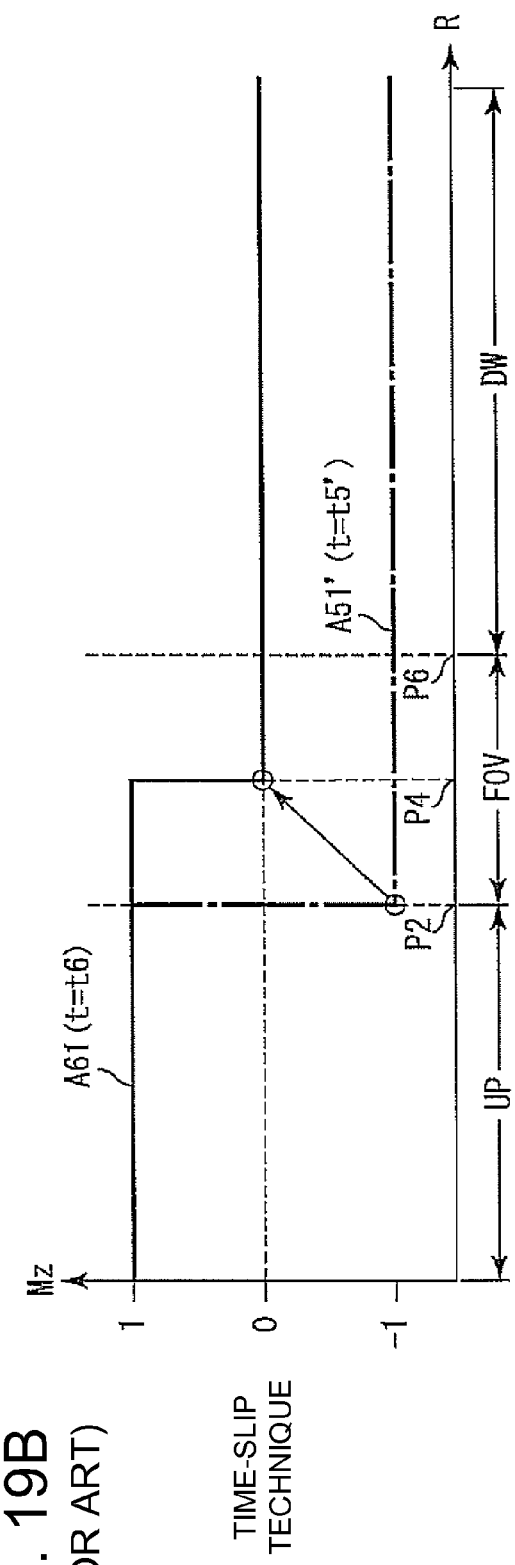

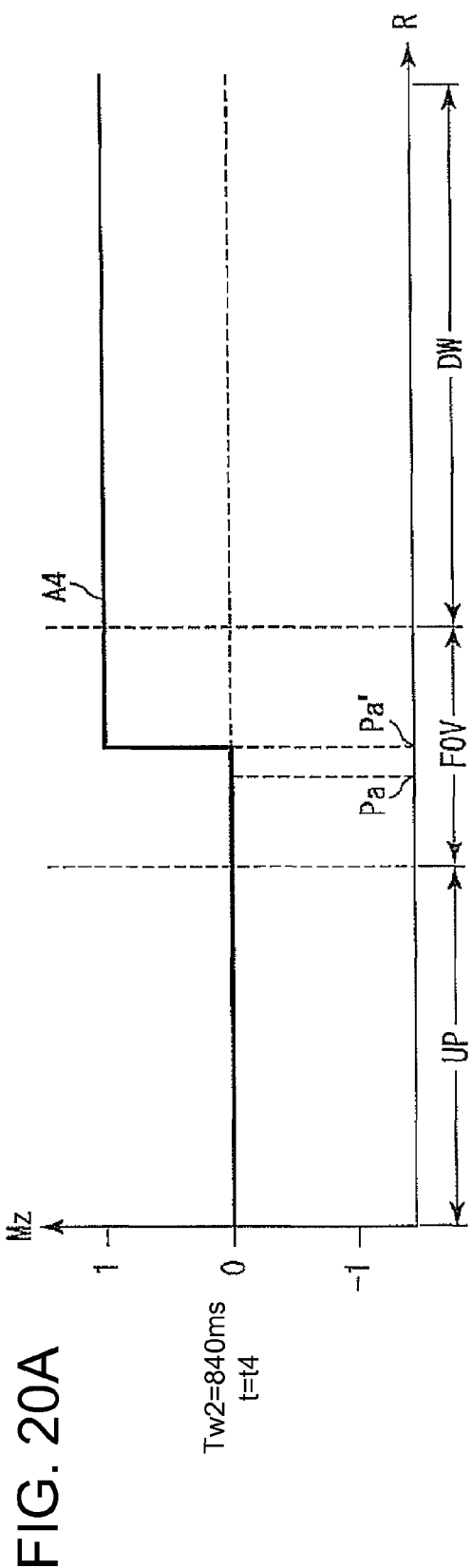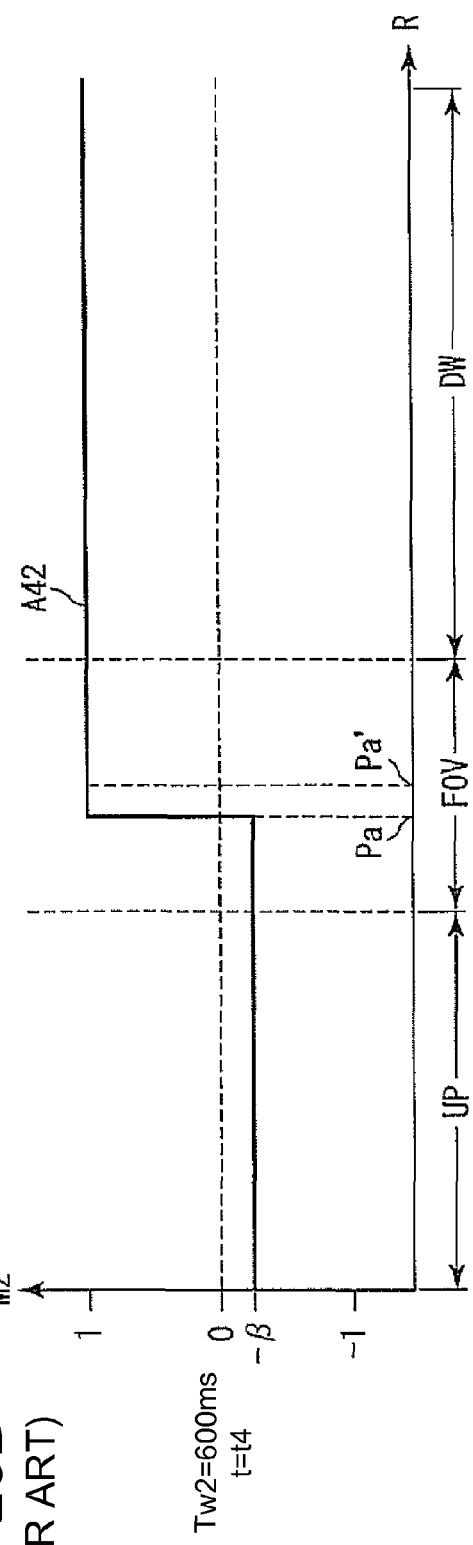
FIG. 20A
FIG. 20B (PRIOR ART)

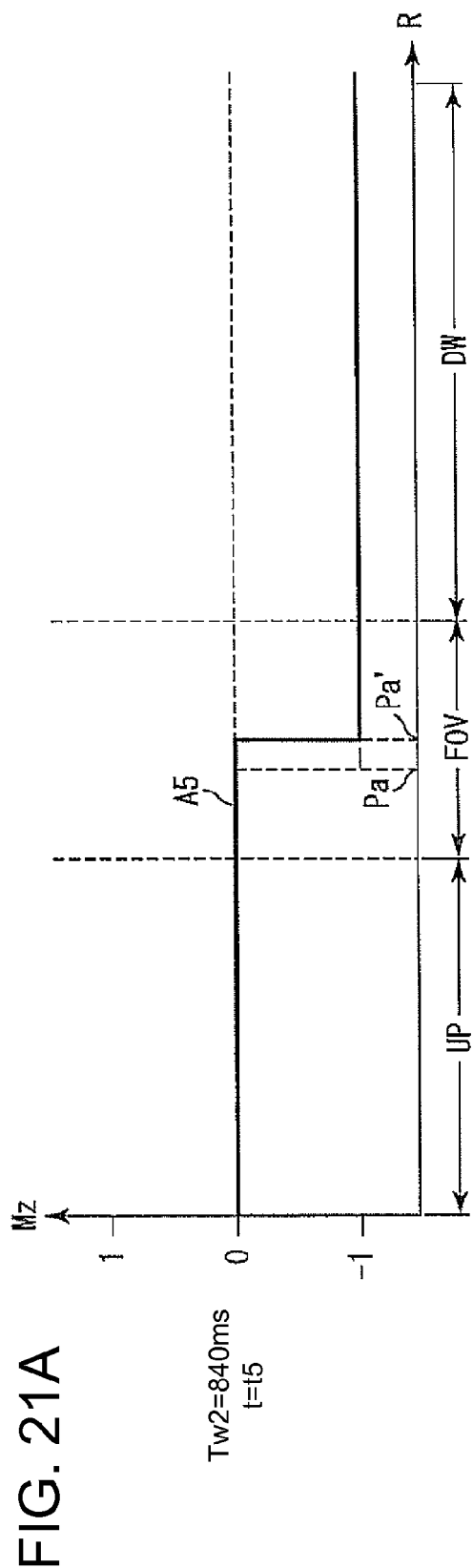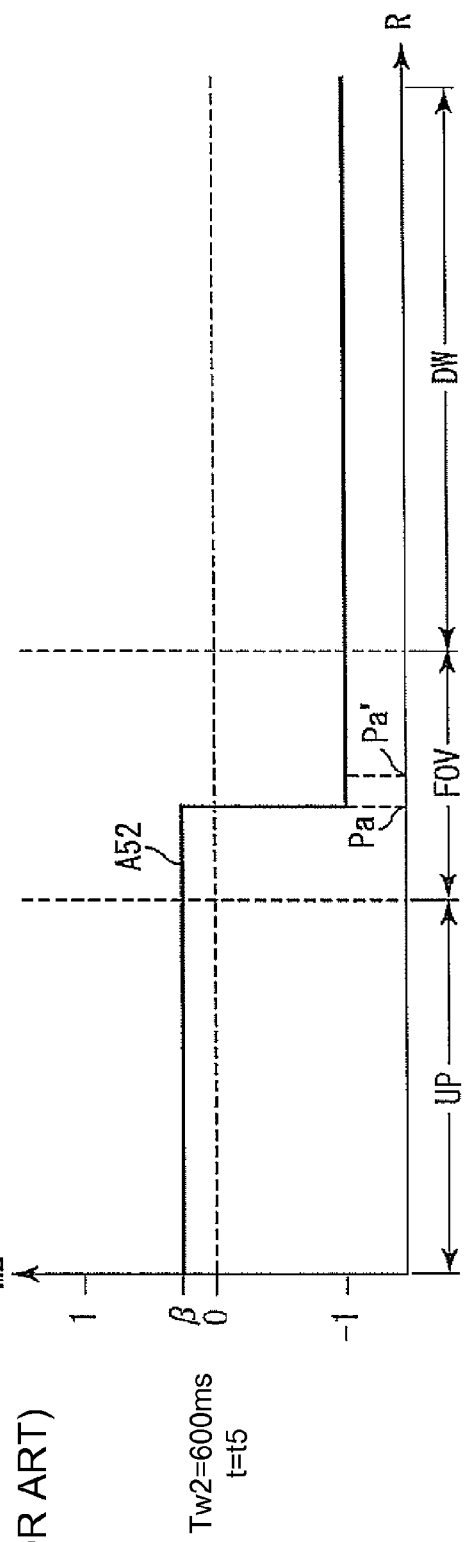

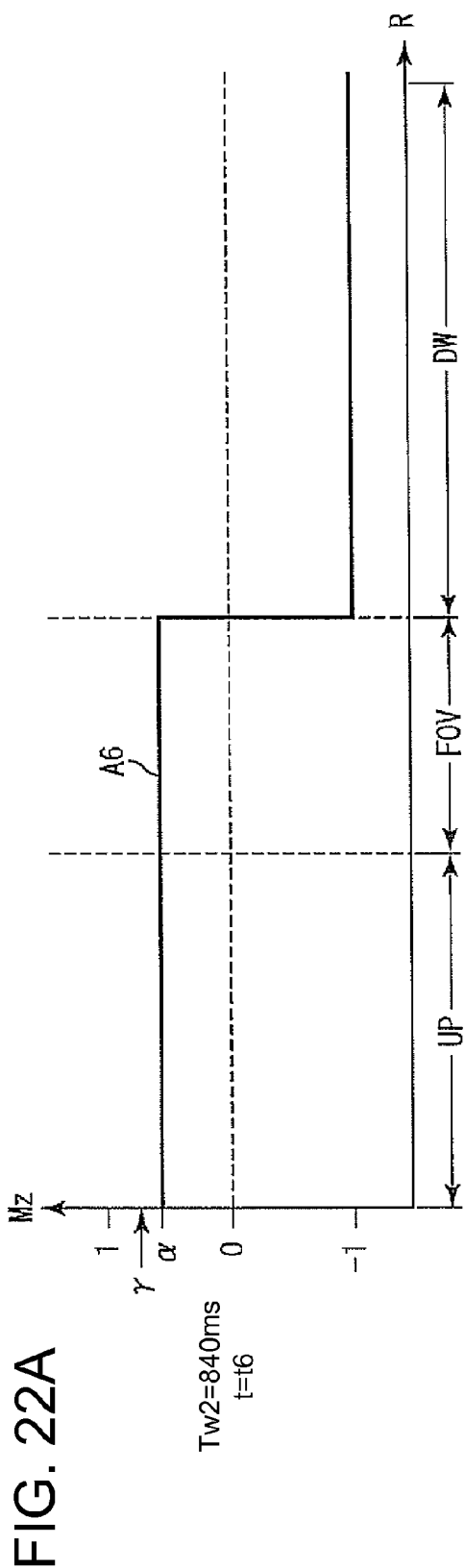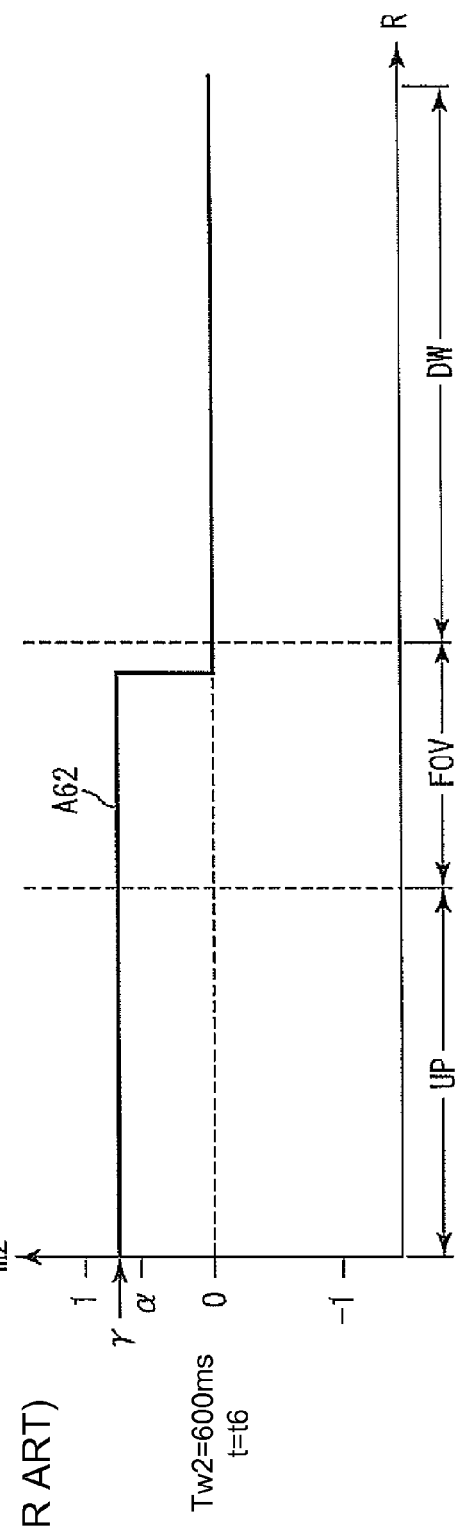
FIG. 22A
FIG. 22B (PRIOR ART)

MRI APPARATUS

CROSS REFERENCE TO RELATED APPLICATIONS

This application claims the benefit of Japanese Patent Application No. 2008-048923 filed Feb. 29, 2008, which is hereby incorporated by reference in its entirety.

BACKGROUND OF THE INVENTION

The embodiments described herein relate to an MRI apparatus for imaging a bodily fluid.

Conventionally, an MRI apparatus is used to image a blood flowing in a blood vessel. For example, the Time-SLIP technique is known as a method of imaging a blood flow (see Mitsue Miyazaki et al: Recent Development of Non-contrast-enhanced MR Angiography, Image Information Medical, Sangyo Kaihatsu Kiko Kabushiki Kaisha September 2006, pp. 952-957).

The method described in the above document may narrow a rendered blood flow range when imaging a patient whose blood flow is slow.

BRIEF DESCRIPTION OF THE INVENTION

It is desirable that the problem described previously is solved.

In a first aspect, the invention provides an MRI apparatus for imaging a subject so as to emphasize, more than a background tissue, a bodily fluid flowing through an imaging region of the subject, the apparatus including: a static magnetic field generating device for generating a static magnetic field to the subject so as to assign positive values to a longitudinal magnetization component of the bodily fluid and a longitudinal magnetization component of the background tissue; a transmission coil for transmitting an RF pulse to the subject; a first transmission coil control device for controlling the transmission coil so that the transmission coil transmits a first inversion pulse for inverting longitudinal magnetization components of the bodily fluid and the background tissue to negative values from the positive values; a second transmission coil control device for controlling the transmission coil so that the transmission coil transmits a second inversion pulse for inverting the longitudinal magnetization component of the background tissue to the positive value from the negative value inverted by the first inversion pulse; a third transmission coil control device for controlling the transmission coil so that the transmission coil transmits a third inversion pulse for inverting the longitudinal magnetization component of the background tissue to the negative value from the positive value inverted by the second inversion pulse; a fourth transmission coil control device for controlling the transmission coil so that the transmission coil transmits an excitation pulse for acquiring data about the bodily fluid; a first inversion pulse transmission control device so as to transmit the second inversion pulse at a time point when a first wait time has elapsed after transmitting the first inversion pulse; a second inversion pulse transmission control device so as to transmit the third inversion pulse at a time point when a second wait time has elapsed after transmitting the second inversion pulse; and a third inversion pulse transmission control device so as to transmit the excitation pulse at a time point when a third wait time elapsed after transmitting the third inversion pulse, wherein the third inversion pulse transmission control device configures the third wait time so that the excitation pulse is transmitted while an absolute value for a longitudinal magnetization component of the first bodily fluid flowing through the imaging region is greater than an absolute value for a longitudinal magnetization component of a background tissue in the imaging region.

In a second aspect, the invention provides a program for an MRI apparatus that images a subject so as to emphasize, more than a background tissue, a bodily fluid flowing through an imaging region of the subject more than a background tissue and includes: a static magnetic field generating device for generating a static magnetic field to the subject so as to assign positive values to a longitudinal magnetization component of the bodily fluid and a longitudinal magnetization component of the background tissue; and a transmission coil for transmitting an RF pulse to the subject. The program allows the MRI apparatus to function as: a first transmission coil control device for controlling the transmission coil so that the transmission coil transmits a first inversion pulse for inverting longitudinal magnetization components of the bodily fluid and the background tissue to negative values from the positive values; a second transmission coil control device for controlling the transmission coil so that the transmission coil transmits a second inversion pulse for inverting the longitudinal magnetization component of the background tissue to the positive value from the negative value inverted by the first inversion pulse; a third transmission coil control device for controlling the transmission coil so that the transmission coil transmits a third inversion pulse for inverting the longitudinal magnetization component of the background tissue to the negative value from the positive value inverted by the second inversion pulse; a fourth transmission coil control device for controlling the transmission coil so that the transmission coil transmits an excitation pulse for acquiring data about the bodily fluid; a first inversion pulse transmission control device so as to transmit the second inversion pulse at a time point when a first wait time has elapsed after transmitting the first inversion pulse; a second inversion pulse transmission control device so as to transmit the third inversion pulse at a time point when a second wait time has elapsed after transmitting the second inversion pulse; and a third inversion pulse transmission control device so as to transmit the excitation pulse at a time point when a third wait time has elapsed after transmitting the third inversion pulse. The third inversion pulse transmission control device configures the third wait time so that the excitation pulse is transmitted while an absolute value for a longitudinal magnetization component of the first bodily fluid flowing through the imaging region is greater than an absolute value for a longitudinal magnetization component of a background tissue in the imaging region.

The MRI apparatus according to the invention uses a first inversion pulse to invert longitudinal magnetization components of a bodily fluid and a background tissue to negative values. A second inversion pulse returns the negative-inverted longitudinal magnetization component of the background tissue to the positive value. A third inversion pulse re-inverts the longitudinal magnetization component to the negative value. Accordingly, the longitudinal relaxation of the bodily fluid progresses to some degree while the longitudinal magnetization component of the background tissue returns to the positive value and is re-inverted to the negative value. The longitudinal magnetization component of the bodily fluid reaches a null point prior to the longitudinal magnetization component of the background tissue. Therefore, the longitudinal magnetization component of the bodily fluid indicates a value larger than the null point when the longitudinal magnetization component of the background tissue approximates to the null point. When data about the bodily fluid is acquired at this time point, the obtained MR image can sufficiently emphasize the bodily fluid by contrast with the background tissue.

The bodily fluid flows by relaxing longitudinally while the longitudinal magnetization component of the background tissue returns to the positive value and re-inverts to the negative value. The longitudinally relaxing bodily fluid flows by further relaxing longitudinally while the longitudinal magnetization component of the background tissue reaches the null point from the negative value. The bodily fluid having the longitudinal magnetization component sufficiently larger than the null point widely spreads in the imaging region until the data acquisition starts. For this reason, the bodily fluid can be widely rendered even in a case of imaging a subject whose bodily fluid flows slowly.

In the invention, the background tissue signifies a concept that contains all tissues of a subject except the bodily fluid to be imaged. According to the invention, the bodily fluid to be imaged may signify an arterial blood and the background tissue may signify venous blood or fat, for example.

Further objects and advantages of the present invention will be apparent from the following description of the preferred embodiments of the invention as illustrated in the accompanying drawings.

BRIEF DESCRIPTION OF THE DRAWINGS

FIGS. 12A and 12B show pulse sequences according to the embodiment and the Time-SLIP technique;

FIGS. 13A and 13B are graphs showing the longitudinal magnetization component of the arterial blood of the subject at time t1 of the pulse sequences shown in FIGS. 12A and 12B;

FIGS. 17A and 17B are graphs showing the longitudinal magnetization component of the arterial blood of the subject at time t5 of the pulse sequences shown in FIGS. 12A and 12B;

FIGS. 18A and 18B are graphs showing the longitudinal magnetization component of the arterial blood of the subject at time t5' of the pulse sequences shown in FIGS. 12A and 12B;

FIGS. 19A and 19B are graphs showing the longitudinal magnetization component of the arterial blood of the subject at time t6 of the pulse sequences shown in FIGS. 12A and 12B;

FIGS. 20A and 20B show the longitudinal magnetization component of the arterial blood at time t4 when the inversion times are set to 840 ms and 600 ms;

FIGS. 21A and 21B show the longitudinal magnetization component of the arterial blood immediately after the third inversion period (time t5 in FIG. 3); and FIGS. 22A and 22B show the longitudinal magnetization component of the arterial blood at the start time of the data acquisition period (time t6 in FIG. 3).

DETAILED DESCRIPTION OF THE INVENTION

Embodiments of the invention will be described in further detail with reference to the accompanying drawings. The invention is not limited to the embodiments described herein.

Figure 1:
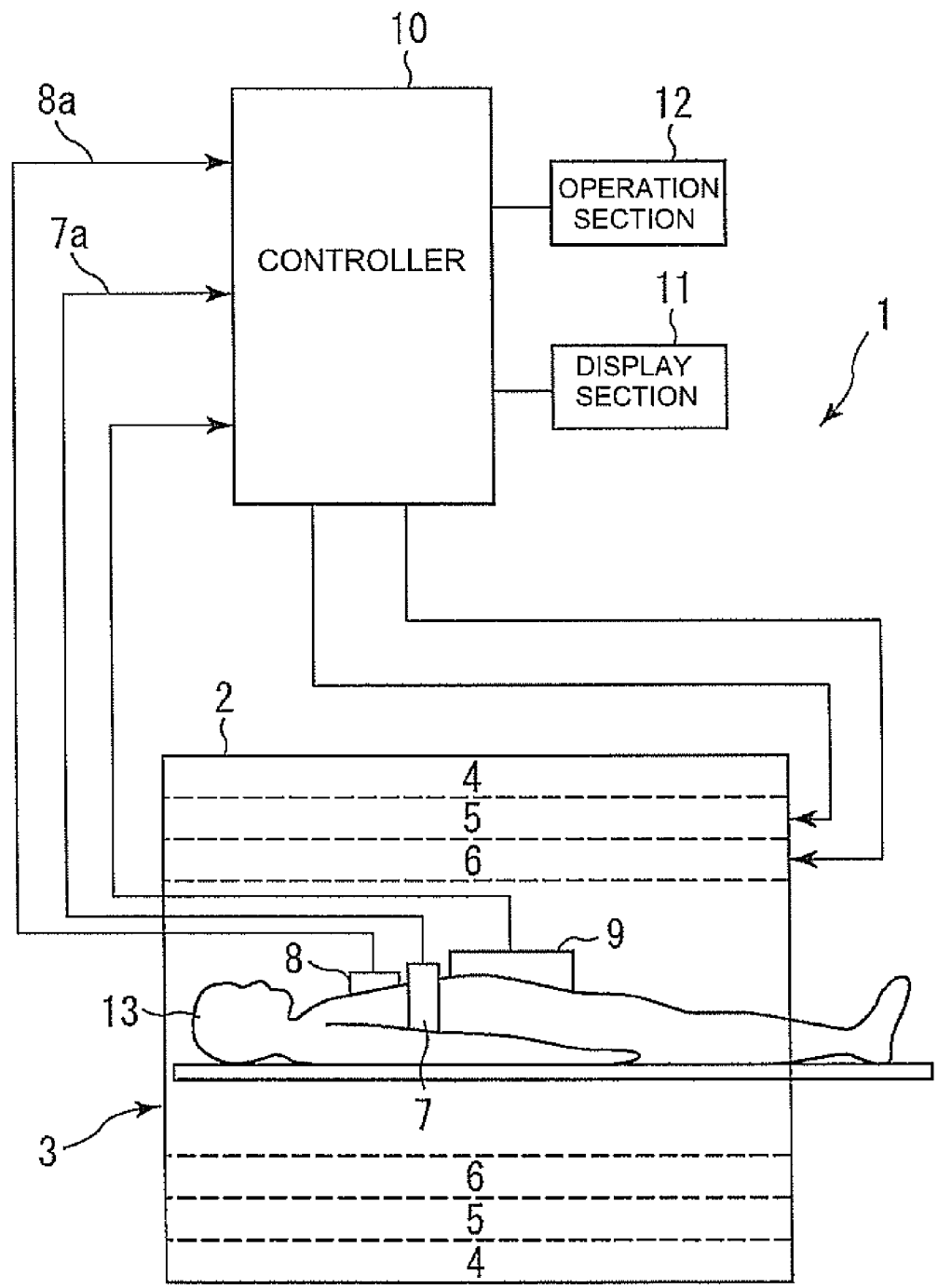
FIG. 1 is an example of a block diagram showing an exemplary MRI apparatus.

FIG. 1 is an example of an MRI (Magnetic Resonance Imaging) apparatus 1. The MRI apparatus 1 is an example of the best mode for embodying the invention.

The MRI apparatus 1 includes a magnet assembly 2. The magnet assembly 2 has a bore 3 for inserting a subject 13. The magnet assembly 2 also includes a static magnetic field generating device 4, a gradient coil 5, and a transmission coil 6.

The static magnetic field generating device 4 generates a constant static magnetic field to the inside of the bore 3. The gradient coil 5 generates a gradient magnetic field in the bore 3. The transmission coil 6 transmits an RF pulse to the inside of the bore 3.

The MRI apparatus 1 includes a bellows 7 and a heartbeat sensor 8.

The bellows 7 detects an aspiration of the subject 13 and transmits an aspiration signal 7a to a controller 10. The heartbeat sensor 8 detects a heartbeat of the subject 13 and transmits an electrocardiographic signal 8a to the controller 10.

The controller 10 computes aspiration and heartbeat states of the subject 13 based on the received aspiration signal 7a and electrocardiographic signal 8a. Based on a computation result, the controller 10 controls the gradient coil 5 and the transmission coil 6. As a result, the gradient coil 5 applies a gradient pulse to the subject 13. The transmission coil 6 transmits a transmission pulse to the subject 13.

The MRI apparatus 1 has a reception coil 9. The reception coil 9 receives an MR signal from the subject 13. The received MR signal is supplied to the controller 10.

The controller 10 reconstructs an image based on the MR signal from the reception coil 9. The reconstructed image is displayed on a display section 11. An operator of the MRI apparatus 1 can interactively operate the MRI apparatus 1 using the display section 11 and an operation section 12.

Figure 2:
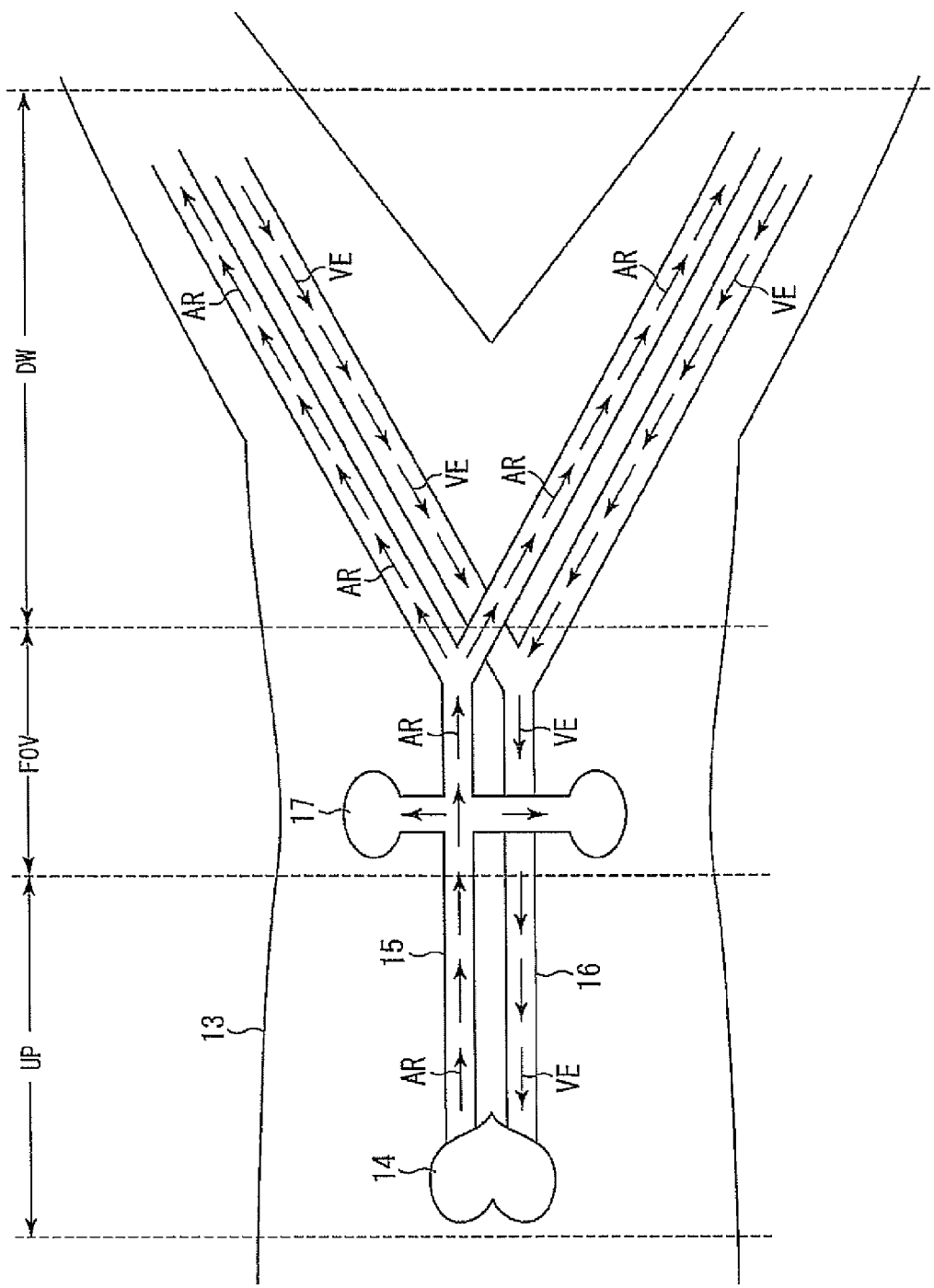
FIG. 2 schematically shows an imaging region of a subject.

FIG. 2 schematically shows an imaging region FOV of the subject 13.

FIG. 2 shows an artery 15 and a vein 16 connecting with a heart 14 of the subject 13. An arterial blood AR flows from an upstream region UP to a downstream region DW via the imaging region FOV. Contrary to the arterial blood AR, the venous blood VE flows from the downstream region DW to the upstream region UP via the imaging region FOV. According to the embodiment, the imaging region FOV includes the kidney 17. The embodiment describes a case of obtaining an MR image of the arterial blood AR flowing through the imaging region FOV.

The venous blood VE as well as the arterial blood AR flows through the imaging region FOV. The imaging region FOV further contains motionless tissues (e.g., a kidney 17). The embodiment aims at imaging the arterial blood AR. It is difficult to visually check a blood flow state of the arterial blood AR when the venous blood VE and the kidney 14 are imaged along with the arterial blood AR. There is a need to possibly avoid rendering tissues (such as the venous blood VE and the kidney 17) not targeted for imaging. The embodiment performs the following pulse sequence to possibly avoid rendering tissues (such as the venous blood VE and the kidney 17) not targeted for imaging.

Figure 3:
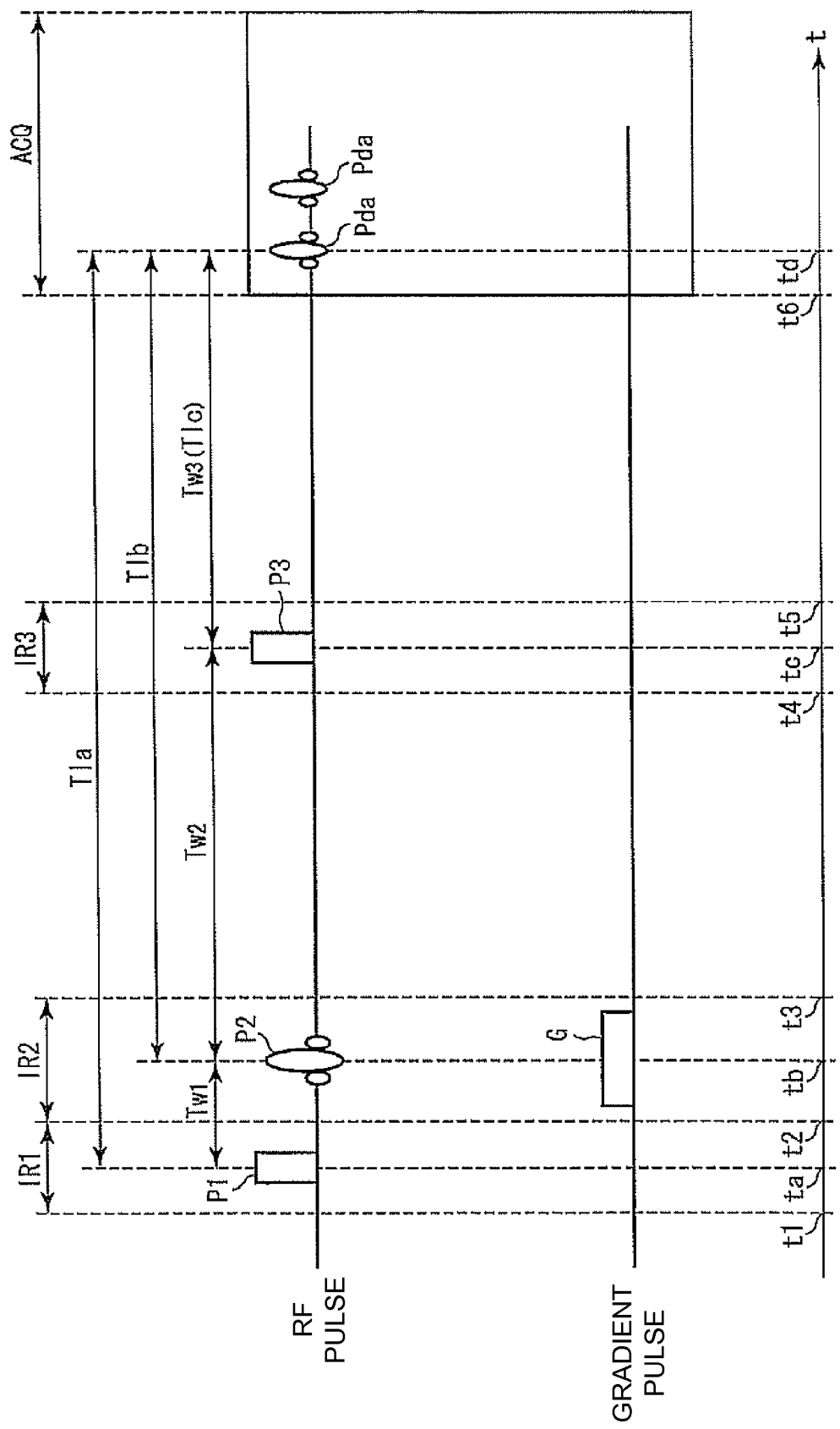
FIG. 3 shows an example of a pulse sequence performed for acquiring an MR image of arterial blood flowing through the imaging region.

FIG. 3 shows an example of the pulse sequence performed for obtaining an MR image of the arterial blood AR flowing through the imaging region FOV.

The pulse sequence 50 includes a first inversion period IR1, a second inversion period IR2, a third inversion period IR3, and a data acquisition period ACQ.

At time ta of the first inversion period IR1, the transmission coil 6 (see FIG. 1) transmits a nonselective RF inversion pulse P1 to the subject 13. The nonselective RF inversion pulse P1 inverts longitudinal magnetization components of tissues (arterial blood AR, venous blood VE, motionless tissue, and the like) in the upstream region UP, the imaging region FOV, and the downstream region DW.

During the second inversion period IR2, the gradient coil 5 (see FIG. 1) applies a gradient pulse G. While the gradient pulse G is applied, the transmission coil 6 transmits a selective RF inversion pulse P2 at time tb. The selective RF inversion pulse P2 is transmitted at a time point when a wait time Tw1 elapses from the nonselective RF inversion pulse P1. The gradient pulse G and the selective RF inversion pulse P2 are adjusted so as to invert longitudinal magnetization components of tissues (arterial blood AR, venous blood VE, motionless tissue, and the like) contained in the imaging region FOV and the downstream region DW (see FIG. 4). The second inversion period IR2 is followed by the third inversion period IR3.

At time tc of the third inversion period IR3, the transmission coil 6 transmits a nonselective RF inversion pulse P3 to the subject 13. The nonselective RF inversion pulse P3 is transmitted at a time point when a wait time Tw2 elapses from the selective RF inversion pulse P2. The third inversion period IR3 is followed by the data acquisition period ACQ.

Data is acquired during the data acquisition period ACQ. During the data acquisition period ACQ, the transmission coil 6 applies many excitation pulses Pda for data acquisition. The excitation pulse Pda is transmitted at a time point when a wait time Tw3 elapses from the nonselective RF inversion pulse P3.

In FIG. 3, TIa denotes an inversion time between the nonselective RF inversion pulse P1 and the excitation pulse Pda; TIb denotes an inversion time between the selective RF inversion pulse P2 and the excitation pulse Pda; and TIc denotes an inversion time between the nonselective RF inversion pulse P3 and the excitation pulse Pda. Accordingly, the wait time Tw1=TIa−TIb; the wait time Tw2=TIb−TIc; and the wait time Tw3=TIc.

The following shows examples of the inversion times TIa, TIb, and TIc.

TIa: 1680 ms
TIb: (1680−Δt) ms
TIc: 840 ms where Δt of TIb is equivalent to several milliseconds, for example.

In this case, the wait times Tw1, Tw2, and Tw3 are defined as follows.

$$Tw1: \Delta t \text{ ms} \tag{1}$$

$$Tw2: 840 \text{ ms} - \Delta t \tag{2}$$

$$Tw3: 840 \text{ ms} \tag{3}$$

The controller 10 is constructed as follows for performing the pulse sequence 50 in FIG. 3.

Figure 4:
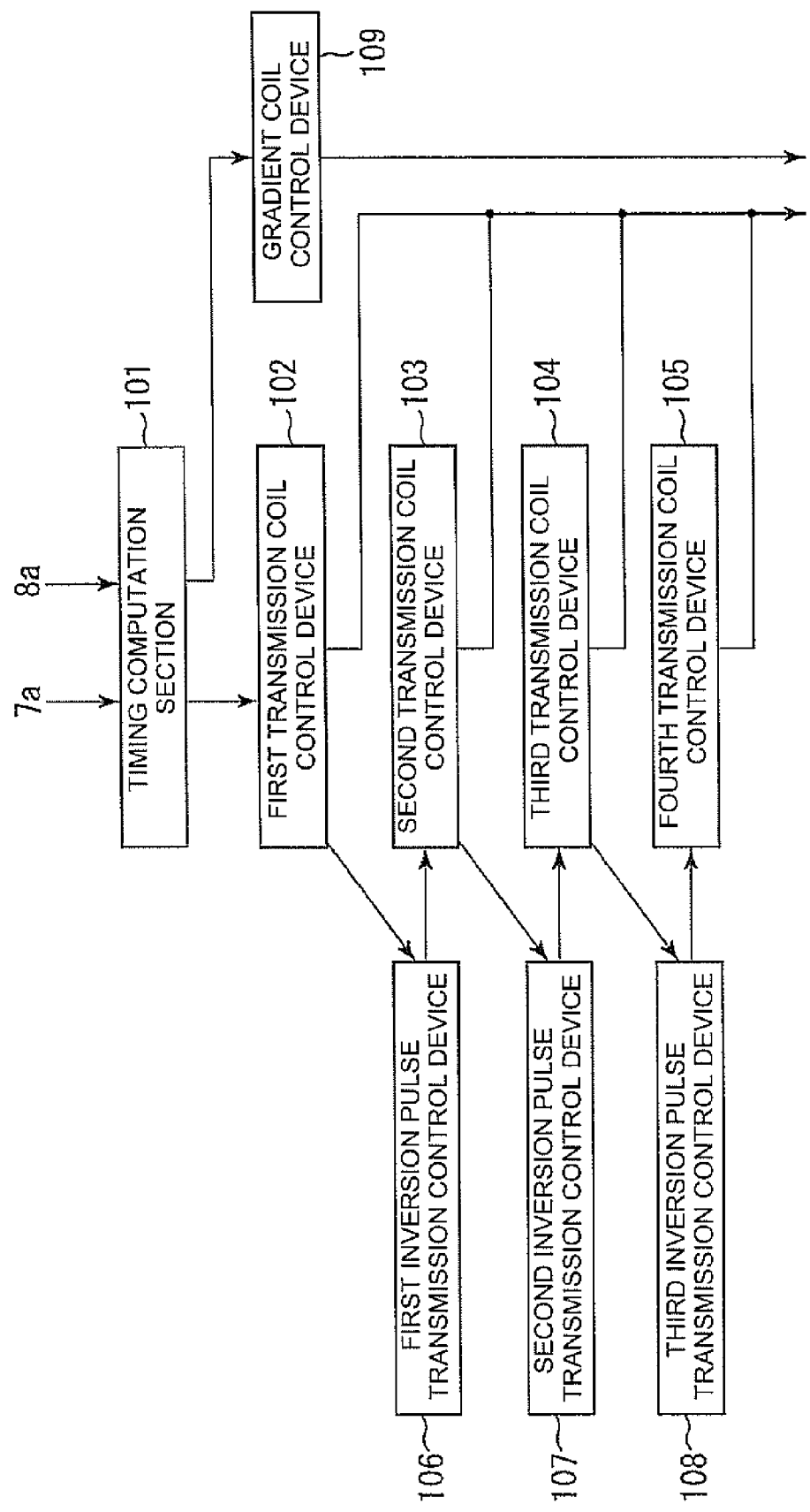
FIG. 4 shows an example of the function block diagram of a controller 10 that may be used with the MRI apparatus shown in FIG. 1.

FIG. 4 is an example of a function block diagram of the controller 10.

The controller 10 includes a timing computation section 101, a first transmission coil control device 102, a second transmission coil control device 103, a third transmission coil control device 104, a fourth transmission coil control device 105, a first inversion pulse transmission control device 106, a second inversion pulse transmission control device 107, a third inversion pulse transmission control device 108, and gradient coil control device 109.

The timing computation section 101 computes a timing for performing the pulse sequence 50 (see FIG. 3) based on the aspiration signal 7a and the electrocardiographic signal 8a. The timing computation section 101 may compute a timing for performing the pulse sequence 50 using only one of the aspiration signal 7a and the electrocardiographic signal 8a. It is possible to perform the pulse sequence 50 without using the aspiration signal 7a and the electrocardiographic signal 8a.

The first transmission coil control device 102 controls the transmission coil 6 so that the transmission coil 6 transmits the nonselective RF inversion pulse P1 (see FIG. 3).

The second transmission coil control device 103 controls the transmission coil 6 so that the transmission coil 6 transmits the selective RF inversion pulse P2 (see FIG. 3).

The third transmission coil control device 104 controls the transmission coil 6 so that the transmission coil 6 transmits the nonselective RF inversion pulse P3 (see FIG. 3).

The fourth transmission coil control device 105 controls the transmission coil 6 so that the transmission coil 6 transmits the excitation pulse Pda for acquiring data about the arterial blood AR.

The first inversion pulse transmission control device 106 controls the second transmission coil control device 103 so that the selective RF inversion pulse P2 is transmitted at a time point when the first wait time Tw1 elapses after transmission of the nonselective inverting RF pulse P1.

The second inversion pulse transmission control device 107 controls the third transmission coil control device 104 so that the nonselective RF inversion pulse P3 is transmitted at a time point when the second wait time Tw2 elapses after transmission of the selective RF inversion pulse P2.

The third inversion pulse transmission control device 108 controls the fourth transmission coil control device 105 so that the excitation pulse Pda is transmitted at a time point when the third wait time Tw3 elapses after transmission of the nonselective RF inversion pulse P3. The third inversion pulse transmission control device 108 configures the third wait time Tw3 so that the excitation pulse Pda is transmitted while a longitudinal magnetization component Mz of the arterial blood AR flowing through the imaging region FOV is larger than a longitudinal magnetization component Mz of the venous blood VE in the imaging region FOV.

The gradient coil control device 109 controls the gradient coil 5 so that the gradient coil 5 applies a gradient pulse G.

The following describes a process the MRI apparatus 1 performs.

Figure 5:
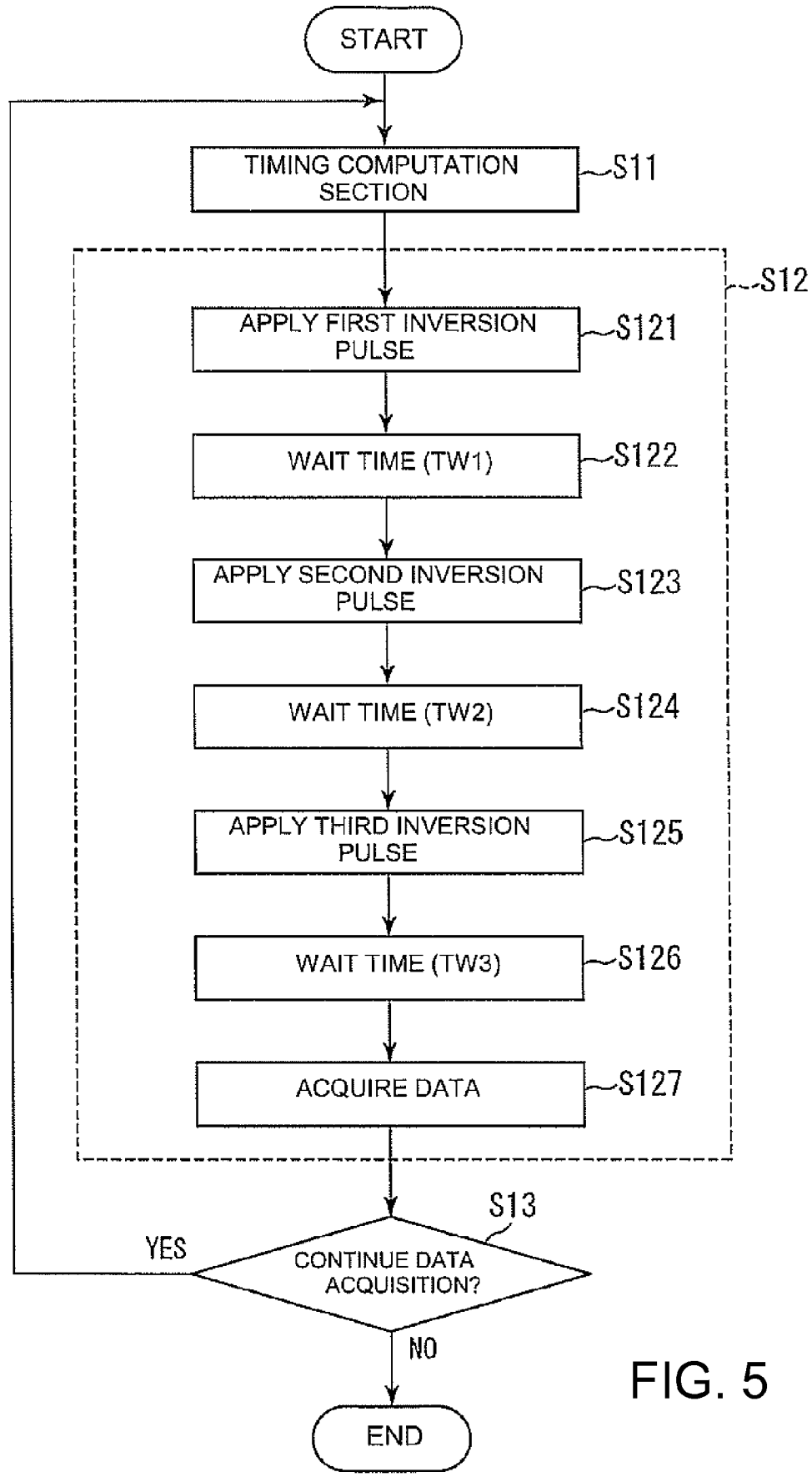
FIG. 5 shows a process flow of the MRI apparatus shown in FIG. 1.
Figure 6:
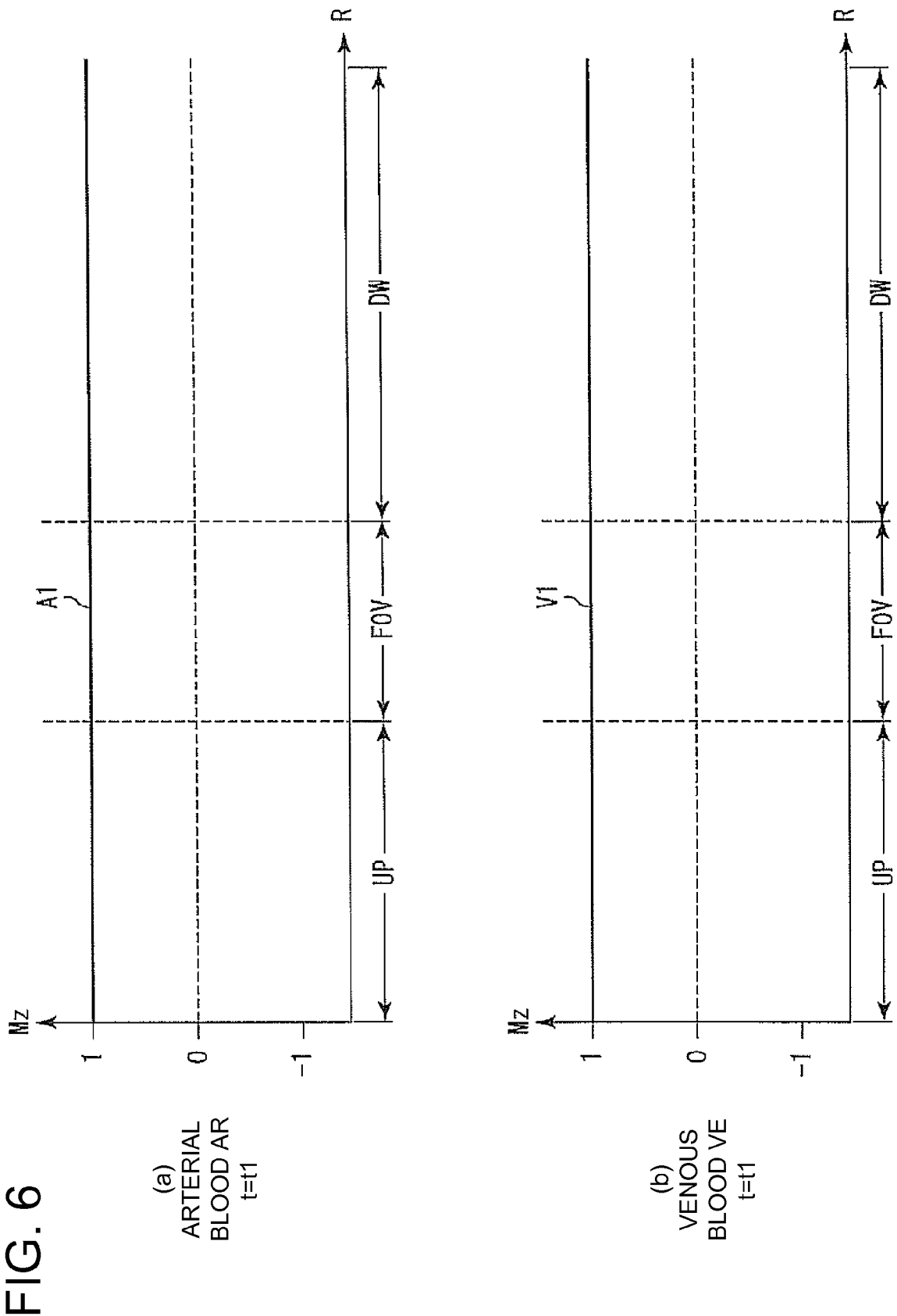
FIGS. 6A and 6B are graphs showing the longitudinal magnetization component of the arterial blood and the venous blood of the subject at time t1 of the pulse sequence shown in FIG. 3.
Figure 7:
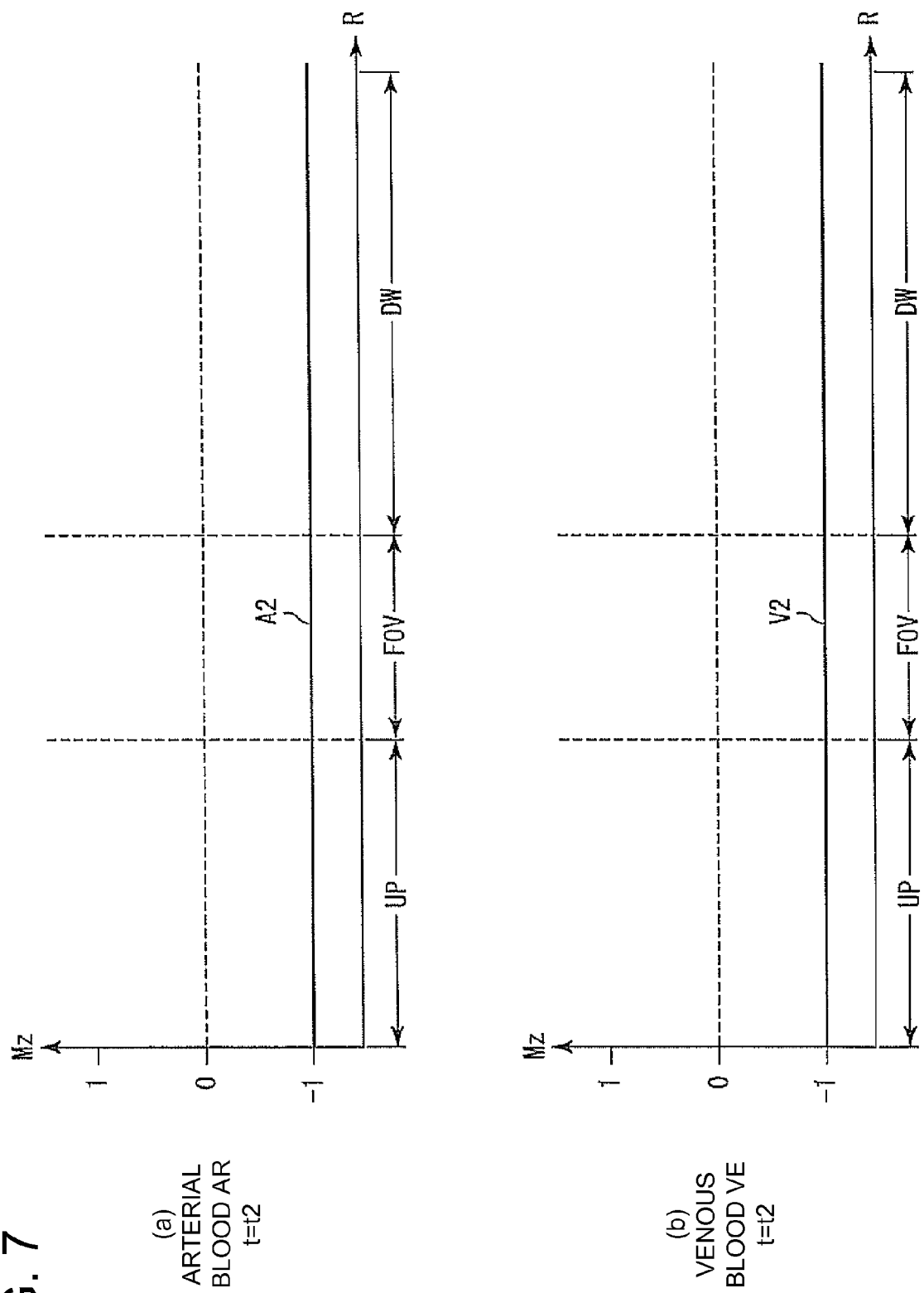
FIGS. 7A and 7B are graphs showing the longitudinal magnetization component of the arterial blood and the venous blood of the subject at time t2 of the pulse sequence shown in FIG. 3.
Figure 8:
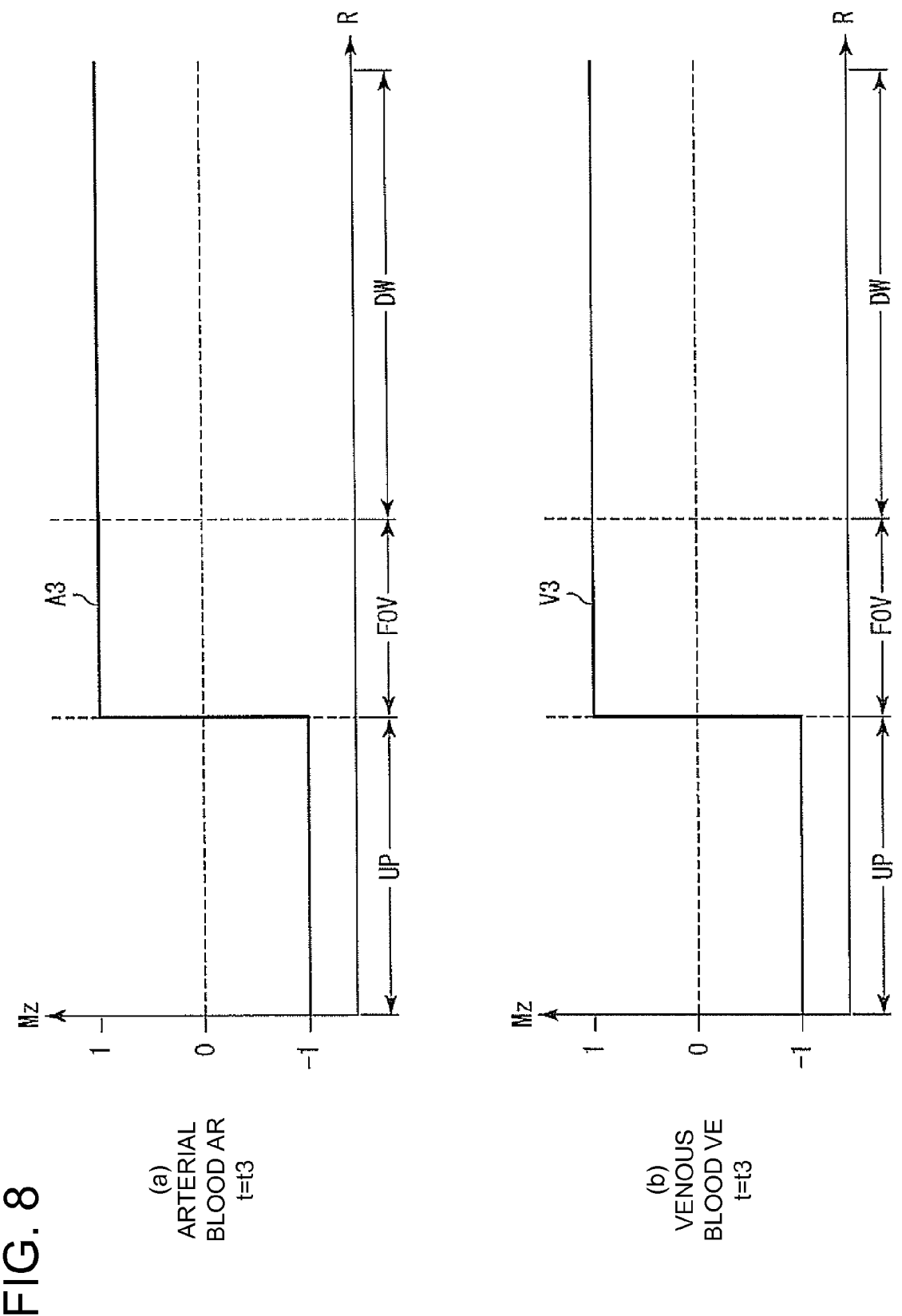
FIGS. 8A and 8B are graphs showing the longitudinal magnetization component of the arterial blood and the venous blood of the subject at time t3 of the pulse sequence shown in FIG. 3.
Figure 9:
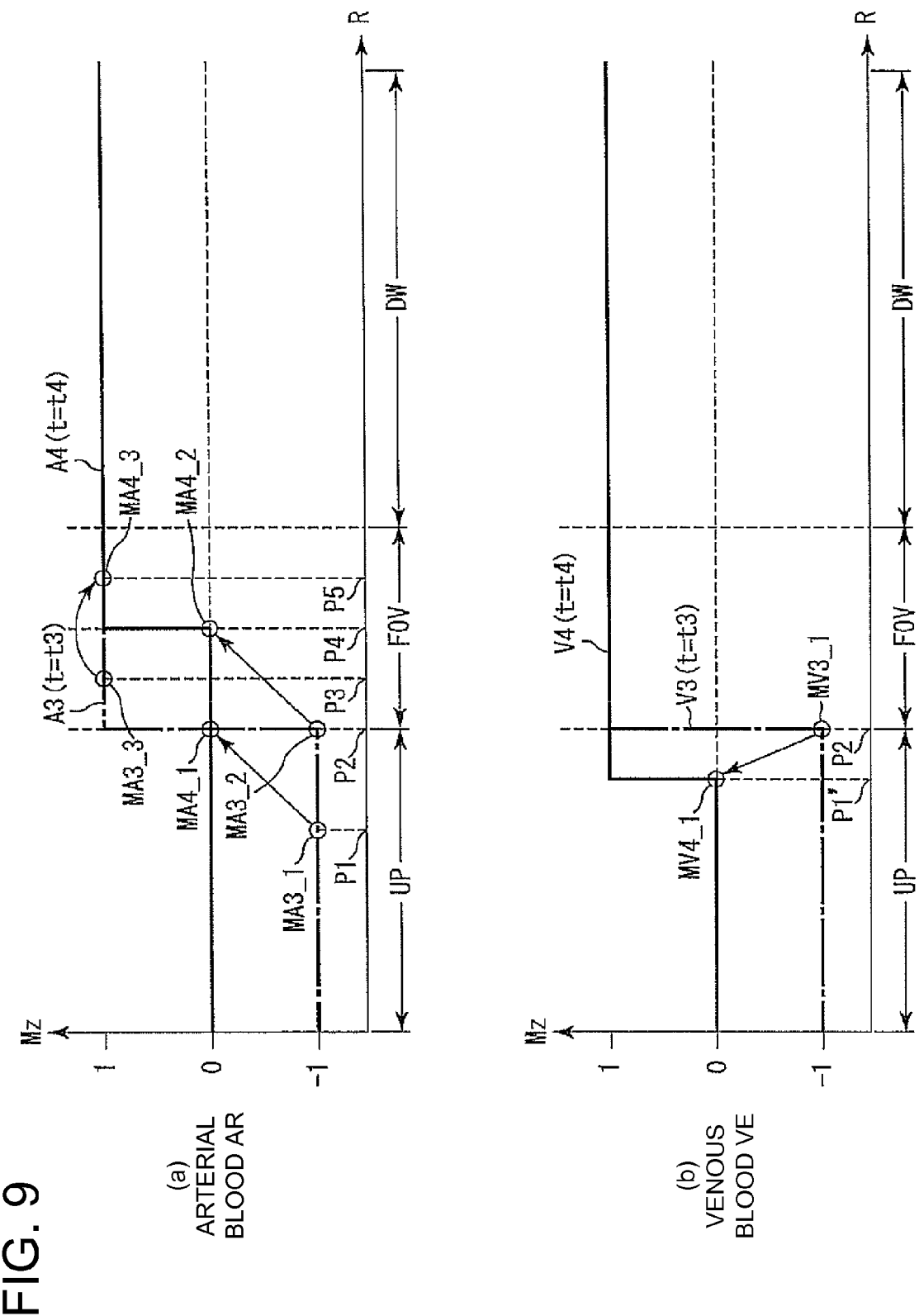
FIGS. 9A and 9B are graphs showing the longitudinal magnetization component of the arterial blood and the venous blood of the subject at time t4 of the pulse sequence shown in FIG. 3.
Figure 10:
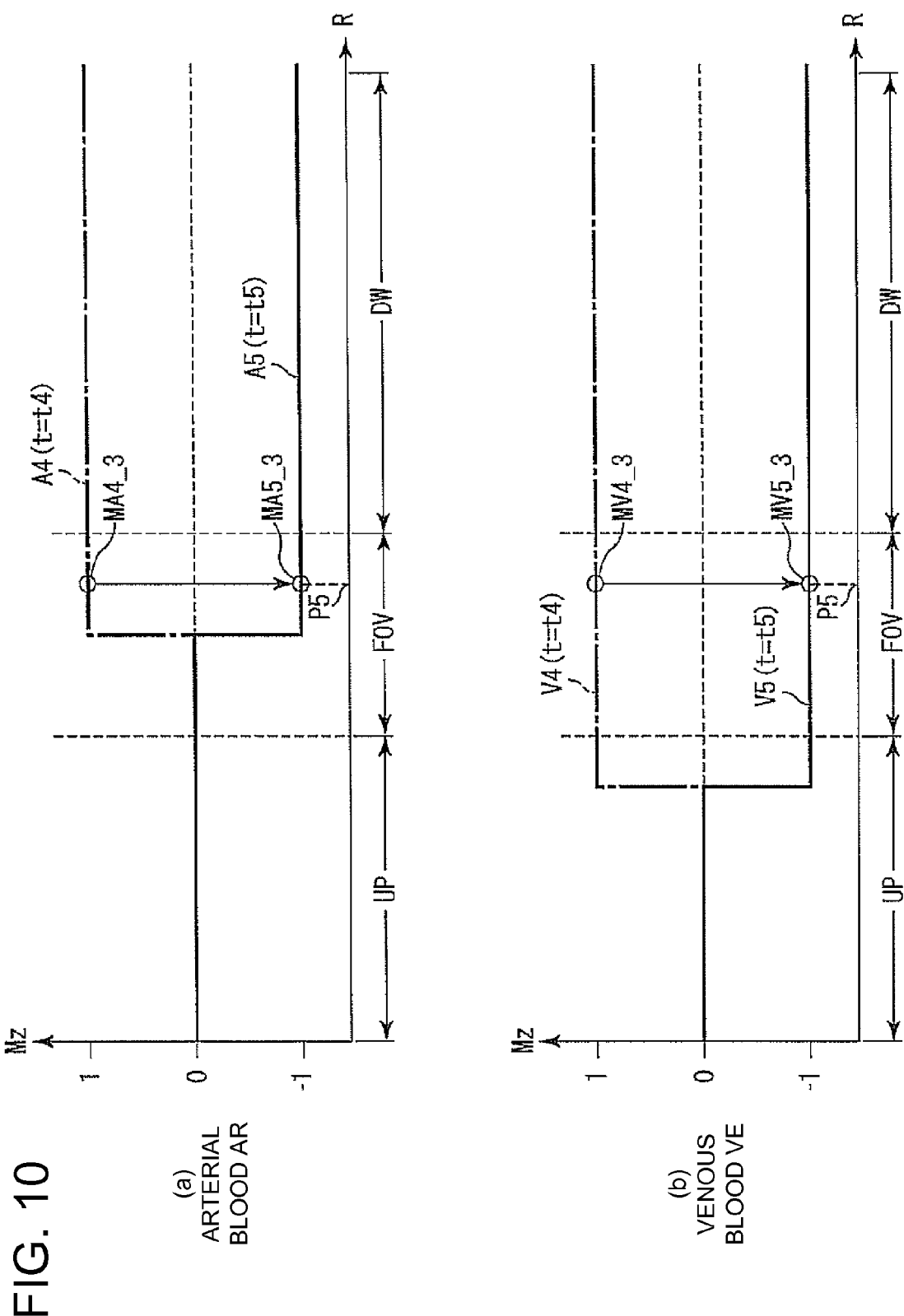
FIGS. 10A and 10B are graphs showing the longitudinal magnetization component of the arterial blood and the venous blood of the subject at time t5 of the pulse sequence shown in FIG. 3.

FIG. 5 is a process flow of the MRI apparatus 1.

At Step S11, the timing computation section 101 (see FIG. 4) computes a timing to perform the pulse sequence 50 (see FIG. 3) based on the aspiration signal 7a and the electrocardiographic signal 8a. After Step S11, the timing computation section 101 proceeds to Step S12.

At Step S12, the timing computation section 101 performs the pulse sequence (see FIG. 3) to acquire data about the arterial blood AR from the imaging region FOV of the subject 13.

After acquiring data about the arterial blood AR at Step S12, the timing computation section 101 proceeds to Step S13 and determines whether or not to continue data acquisition. To continue the data acquisition, the timing computation section 101 returns to Step S11. The loop terminates when it is determined not to continue data acquisition at Step S13.

Step S12 contains seven Sub-steps S121 through S127 for performing the pulse sequence 50 in FIG. 3.

At Sub-step S121, the first transmission coil control device 102 (see FIG. 4) controls the transmission coil 6 so that transmission coil 6 (see FIG. 1) transmits the nonselective RF inversion pulse P1 (see FIG. 3). As a result, the nonselective RF inversion pulse P1 is transmitted at time ta of the first inversion period IR1. At Sub-step S123, the second transmission coil control device 103 (see FIG. 4) controls the transmission coil 6 so that the transmission coil 6 (see FIG. 1) transmits the selective RF inversion pulse P2 (see FIG. 3). As a result, the selective RF inversion pulse P2 is transmitted at time ta of the second inversion period IR2. At Sub-step S125, the third transmission coil control device 104 (see FIG. 4) controls the transmission coil 6 so that the transmission coil 6 transmits the nonselective RF inversion pulse P3 (see FIG. 3). As a result, the nonselective RF inversion pulse P3 is transmitted at time tc of the third inversion period IR3. At Sub-step S127, the fourth transmission coil control device 105 (see FIG. 4) controls the transmission coil 6 so that the transmission coil 6 transmits the excitation pulse Pda for acquiring data about the arterial blood AR.

Step S12 further contains Sub-steps S122, S124, and S126. At Sub-step S122, the first inversion pulse transmission control device 106 (see FIG. 4) controls the second transmission coil control device 103 so that the selective RF inversion pulse P2 is transmitted at a time point when the first wait time Tw1 (=TIa−TIb) elapses after transmission of the nonselective inverting RF pulse P1. At Sub-step S124, the second inversion pulse transmission control device 107 (see FIG. 4) controls the third transmission coil control device 104 so that the nonselective RF inversion pulse P3 is transmitted at a time point when the second wait time Tw2 (=TIb−TIc) elapses after transmission of the selective RF inversion pulse P2. At Sub-step S126, the third inversion pulse transmission control device 108 (see FIG. 4) controls the fourth transmission coil control device 105 so that the excitation pulse Pda is transmitted at a time point when the third wait time Tw3 (=TIc) elapses after transmission of the nonselective RF inversion pulse P3.

The MRI apparatus 1 can obtain a blood flow image with the arterial blood AR emphasized by performing the pulse sequence 50 (see FIG. 3) according to the flow in FIG. 5. With reference to FIGS. 3 and 6 through 11, the following describes why performing the pulse sequence 50 makes it possible to obtain a blood flow image with the arterial blood AR emphasized.

FIGS. 6 through 11 are graphs showing longitudinal magnetization components Mz of the arterial blood AR and the venous blood VE of the subject 13 at time points of the pulse sequence 50 in FIG. 3.

Horizontal axes R of the graphs in FIGS. 6 through 11 indicate the upstream region UP, the imaging region FOV, and the downstream region DW of the subject 13 in FIG. 2. Vertical axes of the graphs in FIGS. 6 through 11 indicate longitudinal magnetization components Mz of the arterial blood AR and the venous blood VE of the subject 13.

Let us consider graphs in FIGS. 6A and 6B.

FIGS. 6A and 6B indicate longitudinal magnetization components Mz of the arterial blood AR and the venous blood VE immediately before the first inversion period IR1 (time t1 in FIG. 3). The graph in FIG. 6A shows a line A1 that represents relation between a region R of the subject 13 and the longitudinal magnetization component Mz of the arterial blood AR at time t1. The graph in FIG. 6B shows a line V1 that represents relation between the region R of the subject 13 and the longitudinal magnetization component Mz of the venous blood VE at time t1.

(1) About the Graph in FIG. 6A

At time t1, the nonselective RF inversion pulse P1 is not transmitted yet. Accordingly, the static magnetic field generating device 4 (see FIG. 1) sets the longitudinal magnetization component Mz of the arterial blood AR to 1 throughout the upstream region UP, the imaging region FOV, and the downstream region DW.

(2) About the Graph in FIG. 6B

The longitudinal magnetization component Mz of the venous blood is also set to 1 throughout the upstream region UP, the imaging region FOV, and the downstream region DW.

The nonselective RF inversion pulse P1 is transmitted immediately after time t1 (see FIG. 3). Transmitting the nonselective RF inversion pulse P1 changes the longitudinal magnetization components Mz of the arterial blood AR and the venous blood VE as shown in FIGS. 7A and 7B.

FIGS. 7A and 7B show the longitudinal magnetization components Mz of the arterial blood AR and the venous blood VE immediately after transmission of the nonselective RF inversion pulse P1 (time t2 in FIG. 3).

The graph in FIG. 7A shows a line A2 that represents relation between the region R of the subject 13 and the longitudinal magnetization component Mz of the arterial blood AR at time t2.

The graph in FIG. 7B shows a line V2 that represents relation between the region R of the subject 13 and the longitudinal magnetization component Mz of the venous blood VE at time t2.

(1) About the Graph in FIG. 7A

The nonselective RF inversion pulse P1 is transmitted during the first inversion period IR1. As indicated by the line A2, the longitudinal magnetization component Mz of the arterial blood AR is inverted to −1 from 1 throughout the upstream region UP, the imaging region FOV, and the downstream region DW.

(2) About the Graph in FIG. 7B

Similarly to the longitudinal magnetization component Mz of the arterial blood AR, the longitudinal magnetization component Mz of the venous blood VE is also inverted to −1 from 1.

The first inversion period IR1 is followed by the second inversion period IR2 (see FIG. 3). The gradient pulse G and the selective RF inversion pulse P2 are applied during the second inversion period IR2. The gradient pulse G and the selective RF inversion pulse P2 are adjusted so as to invert longitudinal magnetization components of tissues in the imaging region FOV and the downstream region DW (see FIG. 2). During the second inversion period IR2, longitudinal magnetization components Mz of the arterial blood AR and the venous blood VE in the imaging region FOV and the downstream region DW change as shown in graphs of FIGS. 8A and 8B.

FIGS. 8A and 8B indicate longitudinal magnetization components Mz of the arterial blood AR and the venous blood VE immediately after transmission of the selective RF inversion pulse P2 (time t3 in FIG. 5). The graph in FIG. 8A shows a line A3 that represents relation between the region R of the subject 13 and the longitudinal magnetization component Mz of the arterial blood AR at time t3. The graph in FIG. 8B shows a line V3 that represents relation between the region R of the subject 13 and the longitudinal magnetization component Mz of the venous blood VE at time t3.

(1) About the Graph in FIG. 8A

The selective RF inversion pulse P2 transmitted during the second inversion period IR2 inverts the longitudinal magnetization component Mz of the arterial blood AR to 1 from −1 in the imaging region FOV and the downstream region DW. The embodiment specifies a very short time such as several milliseconds (see equation (1)) for the wait time Tw1 after the nonselective RF inversion pulse P1 is transmitted until the selective RF inversion pulse P2 is transmitted. Even after the second inversion period IR2 expires, the arterial blood AR in the upstream region UP hardly relaxes longitudinally. Accordingly, the longitudinal magnetization component Mz in the upstream region UP remains −1 at time t3.

(2) About the Graph in FIG. 8B

Similarly to the longitudinal magnetization component Mz of the arterial blood AR, the longitudinal magnetization component Mz of the venous blood VE is also inverted to 1 from −1.

The second inversion period IR2 is followed by the third inversion period IR3 (see FIG. 3). The second wait time Tw2 is provided between the second inversion period IR2 and the third inversion period IR3. The longitudinal relaxation of the arterial blood AR and the venous blood VE proceeds during the second wait time Tw2. As a result, the longitudinal magnetization components Mz of the arterial blood AR and the venous blood VE change as shown in graphs of FIGS. 9A and 9B.

FIGS. 9A and 9B indicate longitudinal magnetization components Mz of the arterial blood AR and the venous blood VE immediately before the third inversion period IR3 (time t4 in FIG. 3).

The graph in FIG. 9A shows a line A4 (solid line) that represents relation between the region R of the subject 13 and the longitudinal magnetization component Mz of the arterial blood AR at time t4. In the graph of FIG. 9A, a dash-dot-line indicates the line A3 in FIG. 8A.

The graph in FIG. 9B shows a line V4 (solid line) that represents relation between the region R of the subject 13 and the longitudinal magnetization component Mz of the venous blood VE at time t4. In the graph of FIG. 9B, a dash-dot-line indicates the line V3 in FIG. 8B.

(1) About the Graph in FIG. 9A

The longitudinal magnetization component Mz of the arterial blood AR in the upstream region UP is set to −1 at time t3 (see line A3). The longitudinal relaxation progresses for the arterial blood AR with Mz set to −1 at time t3 during the second wait time Tw2. According to the embodiment, the wait time Tw2 is almost equal to a time (approximately 840 ms) during which the longitudinal magnetization component Mz set to −1 of the arterial blood AR reaches a null point (see equation (2)). The arterial blood AR with Mz set to −1 at time t3 is virtually subject to longitudinal magnetization recovery to the null point at time t4. The arterial blood AR flows from the upstream region UP to the downstream region DW. The longitudinal magnetization component Mz=−1 on the line A3 (a range to the left of a position P2 on the horizontal axis R) changes to the longitudinal magnetization component Mz=0 on the line A4 (a range to the left of a position P4 on the horizontal axis R). For example, a flow of the arterial blood AR changes a longitudinal magnetization component MA3_1 (a position P1 on the horizontal axis R) on the line A3 to a longitudinal magnetization component MA4_1 (a position P2 on the horizontal axis R) on the line A4. A flow of the arterial blood AR changes a longitudinal magnetization component MA3_2 (the position P2 on the horizontal axis R) on the line A3 to a longitudinal magnetization component MA4_1 (the position P4 on the horizontal axis R) on the line A4.

While the arterial blood AR indicates Mz set to 1 at time t3, the same Mz remains 1 at time t4. The arterial blood AR flows from the upstream region UP to the downstream region DW. The longitudinal magnetization component Mz=1 on the line A3 (a range to the right of the position P2 on the horizontal axis R) changes to the longitudinal magnetization component Mz=1 on the line A4 (a range to the right of the position P4 on the horizontal axis R). For example, a flow of the arterial blood AR changes a longitudinal magnetization component MA3_3 (a position P3 on the horizontal axis R) on the line A3 to a longitudinal magnetization component MA4_3 (a position P5 on the horizontal axis R) on the line A4.

(2) About the Graph in FIG. 9B

The venous blood with Mz set to −1 at time t3 also relaxes longitudinally during the second wait time Tw2. The time for the longitudinal magnetization component Mz of the venous blood VE to reach the null point from Mz=−1 virtually equals that for the arterial blood AR. Accordingly, the venous blood with Mz set to −1 at time t3 is virtually subject to longitudinal magnetization recovery to the null point at time t4. The venous blood VE flows slower than the arterial blood AR in an opposite direction of the arterial blood AR (time t3). The longitudinal magnetization component Mz on the line V3 changes to that on the line V4 (time t4). For example, a flow of the venous blood VE changes a longitudinal magnetization component MV3_1 (the position P2 on the horizontal axis R) on the line V3 to a longitudinal magnetization component MV4_1 (a position P1' on the horizontal axis R) on the line V4.

The nonselective RF inversion pulse P3 is applied immediately after time t4 (see FIG. 3). Applying nonselective RF inversion pulse P3 changes the longitudinal magnetization components Mz of the arterial blood AR and the venous blood as shown in graphs of FIGS. 10A and 10B.

FIGS. 10A and 10B show longitudinal magnetization components Mz of the arterial blood AR and the venous blood VE immediately after transmission of the nonselective RF inversion pulse P3 (time t5 in FIG. 3).

The graph in FIG. 10A shows a line A5 (solid line) that represents relation between the region R of the subject 13 and the longitudinal magnetization component Mz of the arterial blood AR at time t5. In the graph of FIG. 10A, a dash-dot-line indicates the line A4 in FIG. 9A.

The graph in FIG. 10B shows a line V5 (solid line) that represents relation between the region R of the subject 13 and the longitudinal magnetization component Mz of the venous blood VE at time t5. In the graph of FIG. 10B, a dash-dot-line indicates the line V4 in FIG. 9B.

(1) About the Graph in FIG. 10A

The nonselective RF inversion pulse P3 inverts the longitudinal magnetization component Mz=0 of the arterial blood AR on the line A4 (time t4) to Mz=−1. As a result, the longitudinal magnetization component Mz on the line A4 changes to the longitudinal magnetization component Mz on the line A5. Since a time period between times t4 and t5 is sufficiently short, a moving distance of the arterial blood AR from time t4 to time t5 is negligible. For example, the longitudinal magnetization component MA4_3 (position P5 on the horizontal axis R) on the line A4 changes to a longitudinal magnetization component MA5_3 (position P5 on the horizontal axis R) on the line A5.

(2) About the Graph in FIG. 10B

Similarly to the arterial blood AR, the longitudinal magnetization component Mz of the venous blood is inverted to −1 from 1. Accordingly, the longitudinal magnetization component Mz on the line V4 changes to the longitudinal magnetization component Mz on the line V5. Since the time period between times t4 and t5 is sufficiently short, a moving distance of the venous blood VE from time t4 to time t5 is negligible. For example, a longitudinal magnetization component MV4_3 (position P5 on the horizontal axis R) on the line A4 changes to a longitudinal magnetization component MV5_3 (position P5 on the horizontal axis R) on the line A5.

The third inversion period IR3 is followed by the data acquisition period ACQ (see FIG. 3). The third wait time Tw3 is provided between the third inversion period IR3 and the data acquisition period ACQ. Accordingly, the longitudinal magnetization components Mz of the arterial blood AR and the venous blood change during the third wait time Tw3 as shown in graphs of FIGS. 11A and 11B.

FIGS. 11A and 11B indicate longitudinal magnetization components Mz of the arterial blood AR and the venous blood VE immediately before the data acquisition period ACQ (time t6 in FIG. 3).

The graph in FIG. 11A shows a line A6 (solid line) that represents relation between the region R of the subject 13 and the longitudinal magnetization component Mz of the arterial blood AR at time t6. In the graph of FIG. 11A, a dash-dot-line indicates the line A5 in FIG. 10A.

The graph in FIG. 11B shows a line V6 (solid line) that represents relation between the region R of the subject 13 and the longitudinal magnetization component Mz of the venous blood VE at time t6. In the graph of FIG. 11B, a dash-dot-line indicates the line V5 in FIG. 10B.

Figure 11:
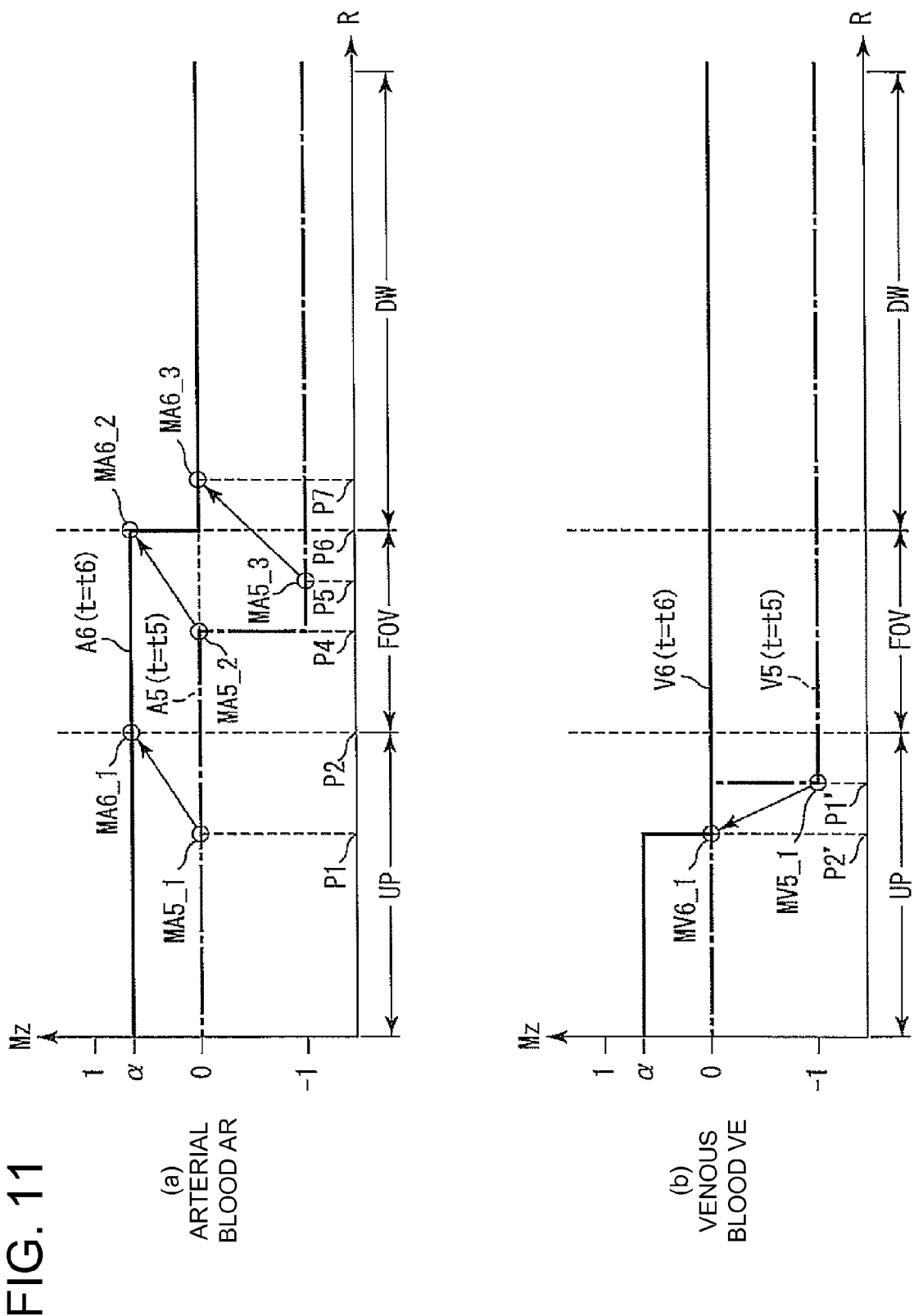
FIGS. 11A and 11B are graphs showing the longitudinal magnetization component of the arterial blood and the venous blood of the subject at time t6 of the pulse sequence shown in FIG. 3.
Figure 14A:
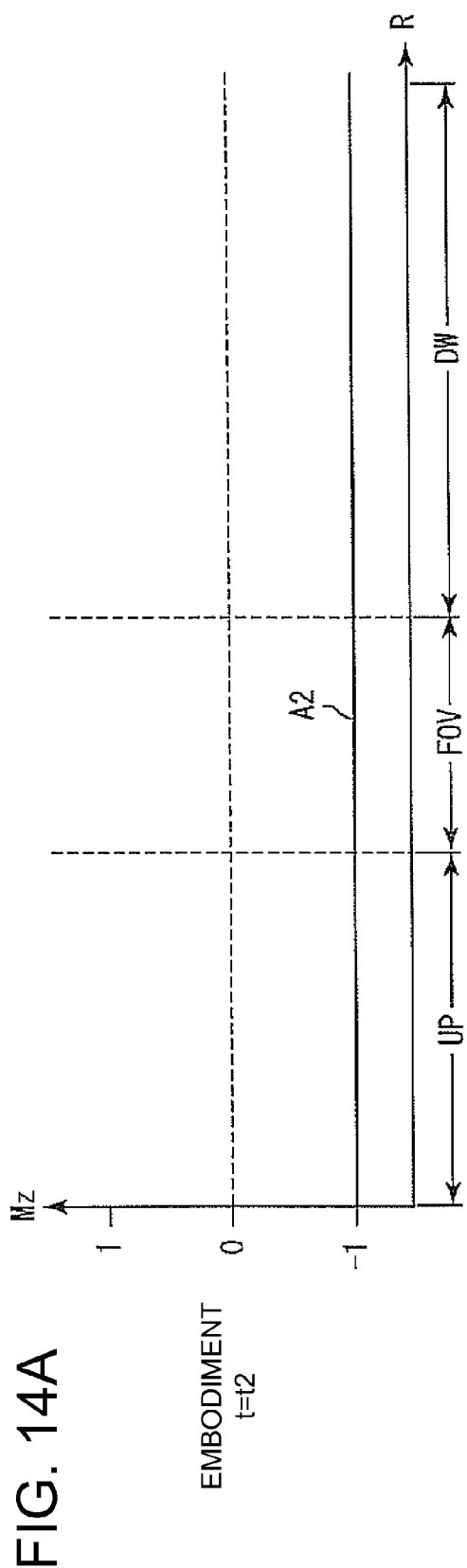
FIGS. 14A and 14B are graphs showing the longitudinal magnetization component of the arterial blood of the subject at time t2 of the pulse sequences shown in FIGS. 12A and 12B.
Figure 14B:
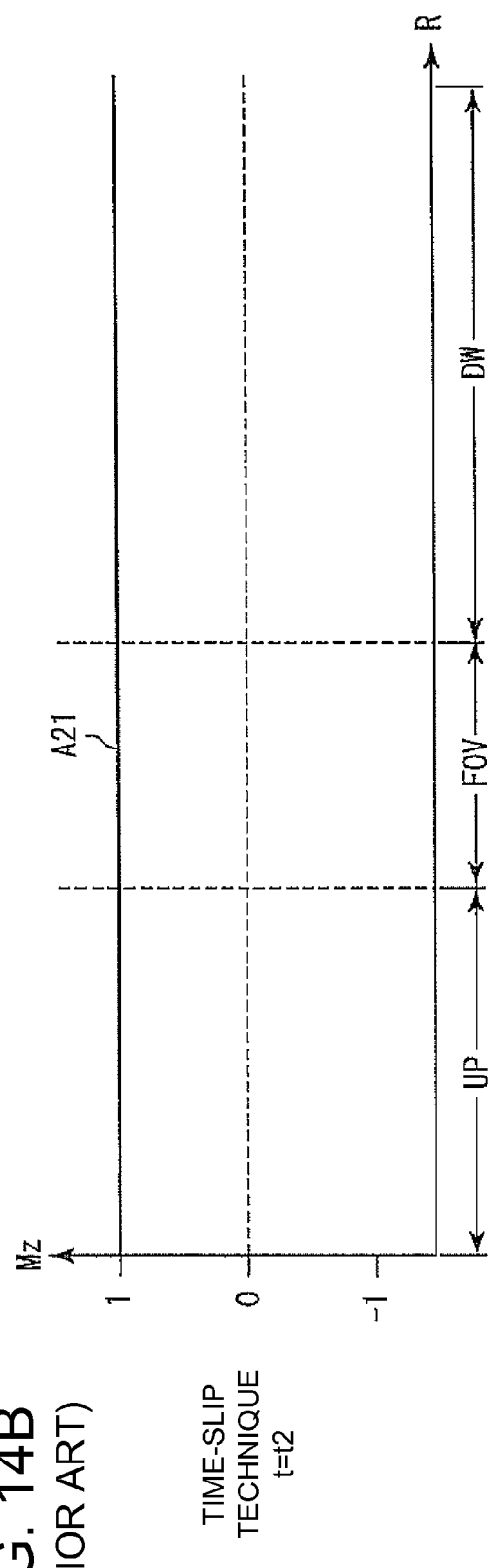

The following describes FIG. 11 in the order of FIG. 11B and then FIG. 11A.

(1) About the Graph in FIG. 11B

The venous blood VE with Mz=−1 at time t5 relaxes longitudinally during the third wait time Tw3. The embodiment sets the third wait time Tw3 to a time (840 ms) during which the longitudinal magnetization component Mz of the venous blood VE reaches the null point from Mz=−1. Accordingly, the longitudinal magnetization component Mz=−1 on the line V5 (a range to the right of the position P1' on the horizontal axis R) relaxes longitudinally during the third wait time Tw3 and virtually reaches the null point immediately before the data acquisition period (time t6). The venous blood VE flows from the downstream region DW to the upstream region UP. The longitudinal magnetization component Mz=−1 on the line V5 (a range to the right of the position P1' on the horizontal axis R) changes to the longitudinal magnetization component Mz=0 on the line V6 (a range to the right of a position P2' on the horizontal axis R). For example, a flow of the venous blood VE changes a longitudinal magnetization component MV5_1 on the line V5 (position P1' on the horizontal axis R) to a longitudinal magnetization component MV6_1 (position P2' on the horizontal axis R) on the line V6. As seen from FIG. 11B, the venous blood VE in the imaging region FOV contains the longitudinal magnetization component Mz set to zero at time t6.

(2) About the Graph in FIG. 11A

The arterial blood AR with Mz=−1 at time t5 also relaxes longitudinally during the third wait time Tw3. The time for the longitudinal magnetization component Mz of the arterial blood AR to reach the null point from Mz=−1 virtually equals that for the venous blood VE. Accordingly, the longitudinal magnetization component Mz=−1 on the line A5 (the range to the right of the position P4 on the horizontal axis R) relaxes longitudinally during the third wait time Tw3 and virtually reaches the null point immediately before the data acquisition period (time t6). The arterial blood AR flows from the upstream region UP to the downstream region DW. The longitudinal magnetization component Mz=−1 on the line A5 (the range to the right of the position P4 on the horizontal axis R) changes to the longitudinal magnetization component Mz=0 on the line A6 (the range to the right of the position P6 on the horizontal axis R). For example, the longitudinal magnetization component MA5_3 on the line A5 (position P5 on the horizontal axis R) changes to the longitudinal magnetization component MA6_3 on the line A5 (position P7 on the horizontal axis R).

The longitudinal magnetization component Mz=0 (the range to the left of the position P4 on the horizontal axis R) is subject to longitudinal magnetization recovery up to $\alpha$ ($0<\alpha<1$) during the third wait time Tw3. The embodiment defines a as approximately 0.5 to 0.6. The arterial blood AR flows from the upstream region UP to the downstream region DW. The longitudinal magnetization component Mz=0 on the line A5 (the range to the left of a position P4 on the horizontal axis R) changes to the longitudinal magnetization component Mz=$\alpha$ (the range to the left of a position P6 on the horizontal axis R) on the line A6. For example, a longitudinal magnetization component MA5_1 on the line A5 (position P1 on the horizontal axis R) changes to a longitudinal magnetization component MA6_1 on the line A6 (position P2 on the horizontal axis R). A longitudinal magnetization component MA5_2 on the line A5 (position P4 on the horizontal axis R) changes to a longitudinal magnetization component MA6_2 on the line A6 (position P6 on the horizontal axis R). As seen from FIG. 11A, the arterial blood AR in the imaging region FOV contains the longitudinal magnetization component Mz set to $\alpha$ (=0.5 to 0.6) greater than zero at time t6.

When comparing FIG. 11A and FIG. 11B with respect to the range of the imaging region FOV, the longitudinal magnetization component Mz of the arterial blood AR is set to $\alpha$ (=0.5 to 0.6) on the line A6, and longitudinal magnetization component Mz of the venous blood VE is set to zero on the line V6. Accordingly, performing the pulse sequence 50 in FIG. 3 can obtain a blood flow image with the arterial blood AR emphasized.

For example, the Time-SLIP technique is known as a technique of separating artery and vein from each other. However, this Time-SLIP technique images the arterial blood AR only in a range narrower than the imaging region FOV obtained in the embodiment. The reason is described below by comparing the embodiment and the Time-SLIP technique.

FIGS. 12A and 12B show pulse sequences according to the above-mentioned embodiment and the Time-SLIP technique.

FIG. 12A shows the pulse sequence 50 according to embodiment (see FIG. 3). FIG. 12B shows an example of a pulse sequence according to the Time-SLIP technique.

A pulse sequence 51 according to the Time-SLIP technique is provided with the third inversion period IR3 at the same timing as the pulse sequence 50 according to the embodiment of the invention. The pulse sequence of the Time-SLIP technique is not provided with the first inversion period IR1 and the second inversion period IR2, but with a fourth inversion period IR4 immediately after the third inversion period IR3 instead.

The following describes how performing the pulse sequences 50 and 51 change the longitudinal magnetization component of the arterial blood AR.

FIGS. 13 through 19 are graphs showing the longitudinal magnetization component Mz of the arterial blood AR of the subject 13 at time points of the pulse sequences 50 and 51 in FIGS. 12.

Horizontal axes R of the graphs in FIGS. 13 through 19 indicate the upstream region UP, the imaging region FOV, and the downstream region DW of the subject 13 in FIG. 2. Vertical axes of the graphs in FIGS. 13 through 19 indicate longitudinal magnetization components Mz of the arterial blood AR and the venous blood VE of the subject 13.

Graphs A in FIGS. 13 through 19 show longitudinal magnetization components Mz of the arterial blood AR at time points for performing the pulse sequence 50 (see FIG. 12A) according to the embodiment. Graphs B in FIGS. 13 through 19 show longitudinal magnetization components Mz of the arterial blood AR at time points for performing the pulse sequence 51 (see FIG. 12B) according to the Time-SLIP technique.

The pulse sequence 51 according to the Time-SLIP technique applies no pulse until time t4. Accordingly, as shown in the graphs B of FIGS. 13 through 16, the Time-SLIP technique assigns 1 to the longitudinal magnetization component Mz of the arterial blood AR at times t1 to t4 throughout the upstream region UP, the imaging region FOV, and the downstream region DW.

The third inversion period IR3 starts immediately after time t4.

The nonselective RF inversion pulse P3 is applied during the third inversion period IR3. When the nonselective RF inversion pulse P3 is applied, the longitudinal magnetization component Mz of the arterial blood AR changes as shown in the graph of FIGS. 17A and 17B.

FIGS. 17A and 17B show the longitudinal magnetization component Mz of the arterial blood AR immediately after the second inversion period IR3 (time t5 in FIGS. 12A and 12B).

FIG. 17A is the graph according to the embodiment and shows the line A5 (solid line) that represents relation between the region R of the subject 13 and the longitudinal magnetization component Mz of the arterial blood AR at time t5. In the graph of FIG. 17A, a dash-dot-line indicates the line A4 in FIG. 16A.

FIG. 17B is the graph according to the Time-SLIP technique and shows a line A51 (solid line) that represents relation between the region R of the subject 13 and the longitudinal magnetization component Mz of the arterial blood AR at time t5. In the graph of FIG. 17B, a dash-dot-line indicates a line A41 in FIG. 16B.

Figure 15A:
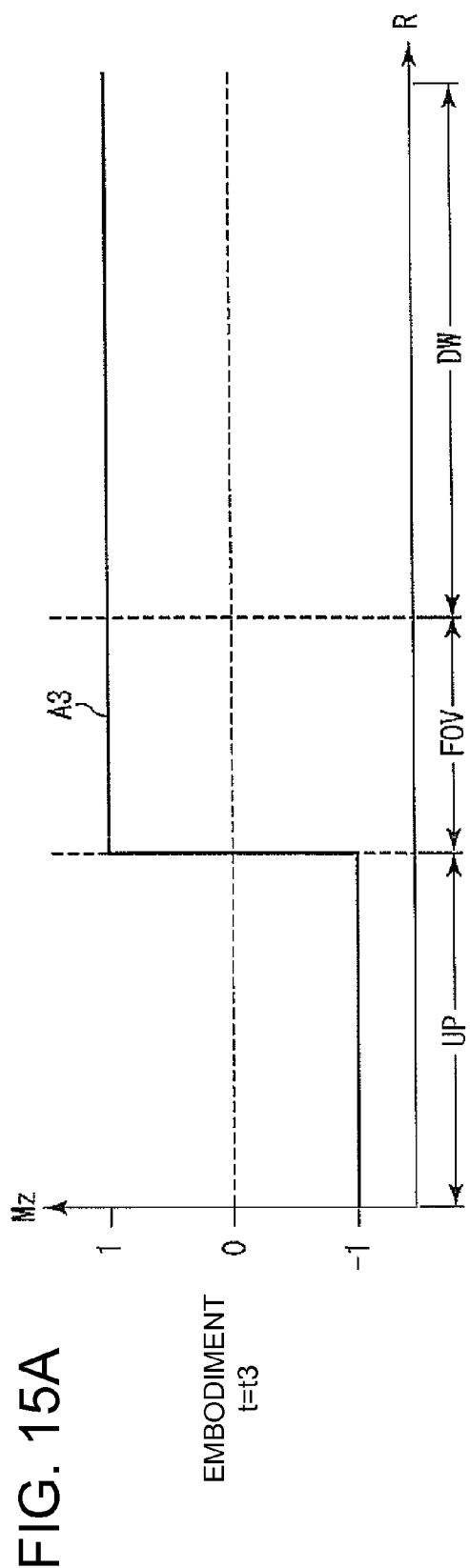
FIGS. 15A and 15B are graphs showing the longitudinal magnetization component of the arterial blood of the subject at time t3 of the pulse sequences shown in FIGS. 12A and 12B.
Figure 15B:
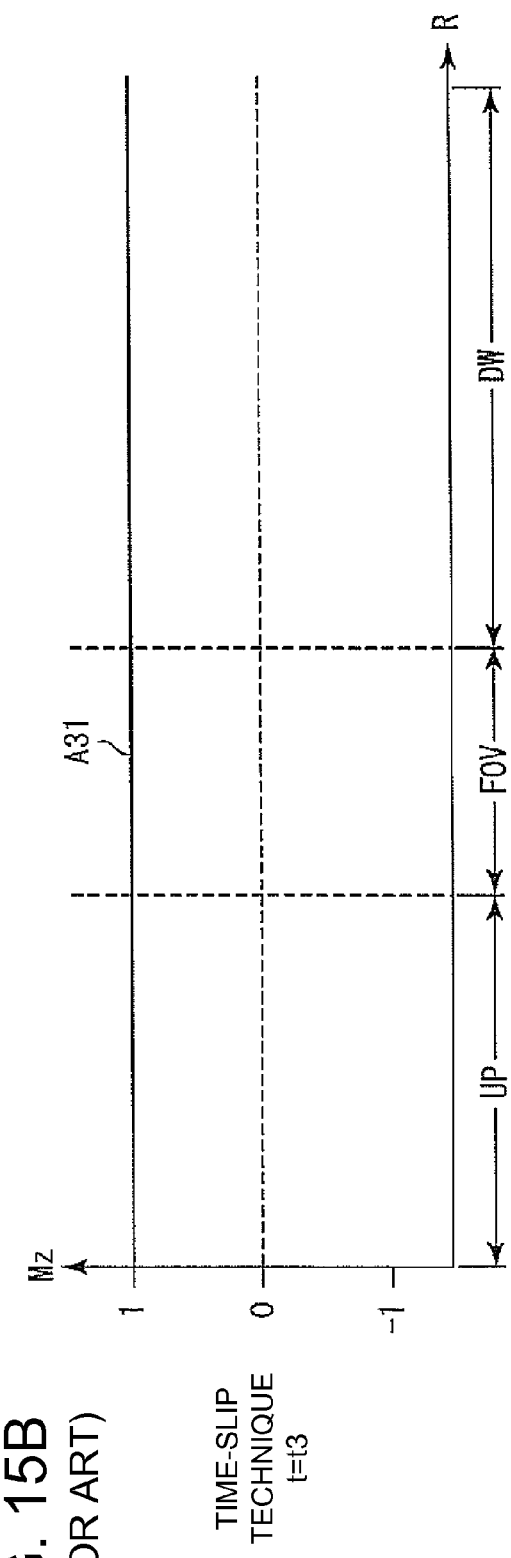
Figure 16A:
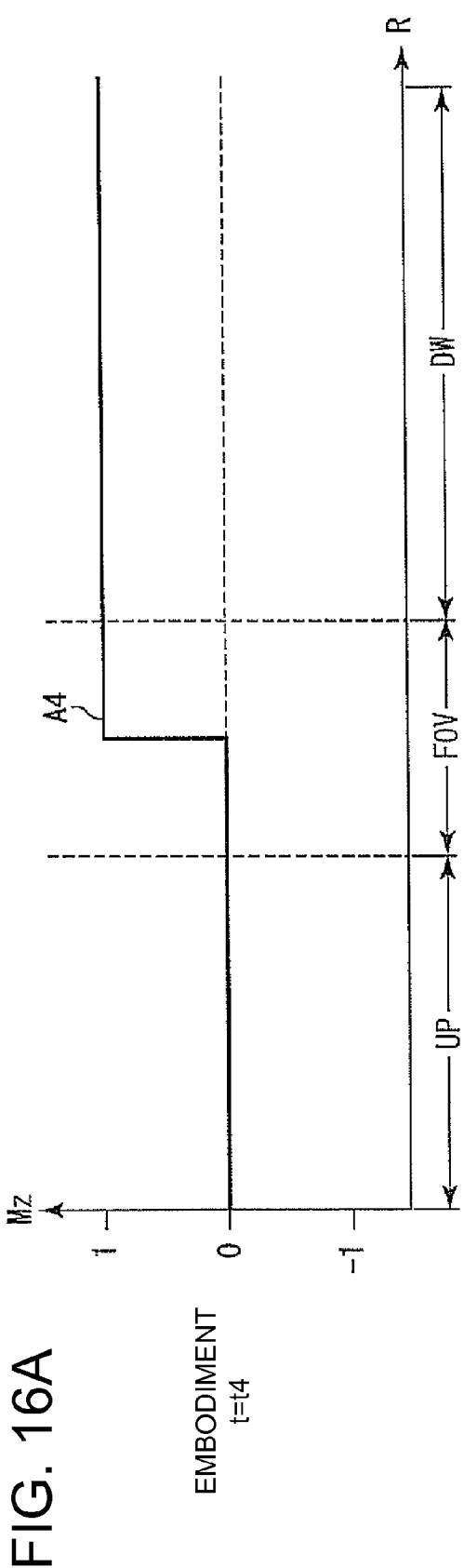
FIGS. 16A and 16B are graphs showing the longitudinal magnetization component of the arterial blood of the subject at time t4 of the pulse sequences shown in FIGS. 12A and 12B.
Figure 16B:
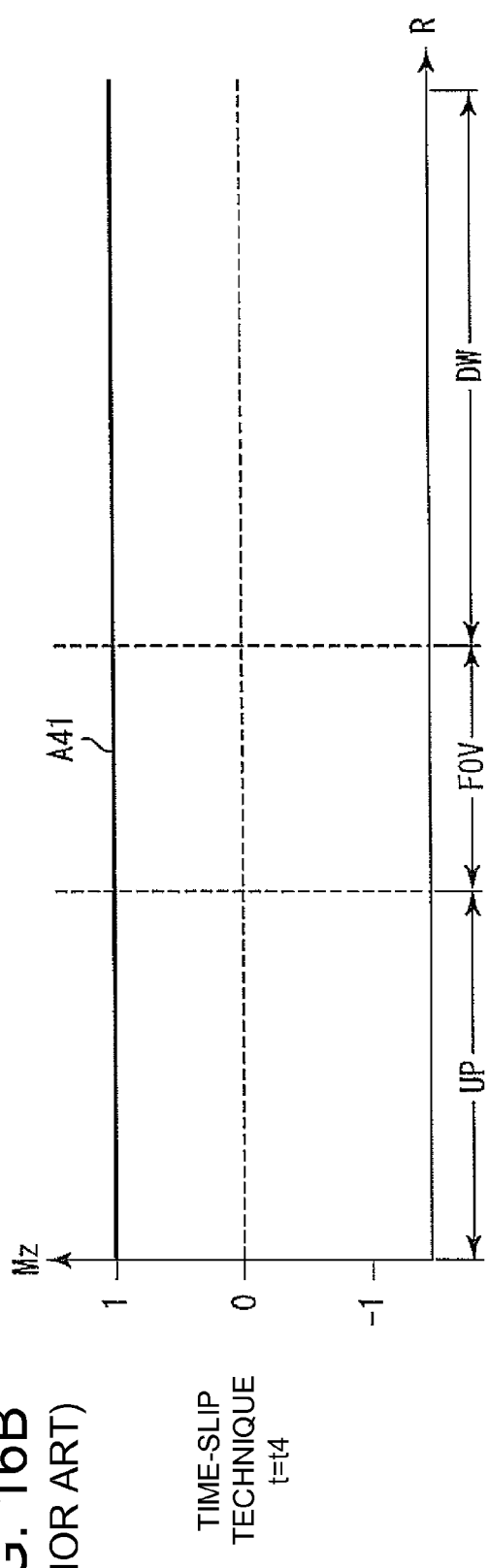

When a nonselective RF inversion pulse P3 is applied during the third inversion period IR3, the longitudinal magnetization component Mz of the tissue of the subject 13 is inverted throughout the upstream region UP, the imaging region FOV, and the downstream region DW. As a result, the longitudinal magnetization component Mz of the arterial blood AR is inverted to −1 from 1. In FIG. 17A (according to the embodiment), the line A4 changes to the line A5. In FIG. 15B (according to the Time-SLIP technique), the line A41 changes to the line A51. When comparing FIGS. 17A with 17B, in FIG. 17A, the longitudinal magnetization component Mz is set to not only −1 but also 0 in the imaging region FOV, and in FIG. 17B, the longitudinal magnetization component Mz is set to −1 throughout the entire imaging region FOV.

The Time-SLIP technique provides the fourth inversion period IR4 immediately after the third inversion period IR3. The gradient pulse G is applied to the subject 13 during the fourth inversion period IR4. The selective RF inversion pulse P4 is transmitted while the gradient pulse G is applied. The gradient pulse G and the selective RF inversion pulse P4 are adjusted so as to invert longitudinal magnetization components of the tissues (e.g., arterial blood AR, venous blood VE, and motionless tissue) in the upstream region UP (see FIG. 2). When the selective RF inversion pulse P4 is transmitted to the fourth inversion period IR4, the Time-SLIP technique changes the longitudinal magnetization component Mz of the arterial blood AR as shown in the graph of FIGS. 18A and 18B.

FIGS. 18A and 18B show longitudinal magnetization components Mz of the arterial blood AR at time t5'.

FIG. 18A is a graph showing the longitudinal magnetization component Mz of the arterial blood AR at time t5' according to the embodiment. FIG. 18B is a graph showing the longitudinal magnetization component Mz of the arterial blood AR at time t5' according to the Time-SLIP technique.

The Time-SLIP technique inverts the longitudinal magnetization direction of a tissue in the upstream region UP during the fourth inversion period IR4. As shown in FIG. 18B, the longitudinal magnetization component Mz of the arterial blood AR is inverted to 1 from −1 in the upstream region UP.

By contrast, the embodiment does not apply the selective RF inversion pulse P4 between times t5 and t5'. According to the embodiment, a graph A5' at time t5' is virtually the same as the graph A5 (see FIG. 17A) at time t5. Since a time period between times t5 and t5' is sufficiently short (several milliseconds), a moving distance of the arterial blood AR from time t5 to time t5' is negligible. The data acquisition period ACQ starts after time t5'.

FIGS. 19A and 19B indicate longitudinal magnetization components Mz of the arterial blood AR immediately before the data acquisition period ACQ (time t6 in FIGS. 12A and 12B).

FIG. 19A is a graph showing the longitudinal magnetization component Mz of the arterial blood AR at time t6 according to the embodiment. FIG. 19B is a graph showing the longitudinal magnetization component Mz of the arterial blood AR at time t6 according to the Time-SLIP technique.

FIG. 19A is the graph according to the embodiment and shows the line A6 (solid line) that represents relation between the region R of the subject 13 and the longitudinal magnetization component Mz of the arterial blood AR at time t6. In the graph of FIG. 19A, a dash-dot-line indicates a line A5' in FIG. 18A.

FIG. 19B is the graph according to the Time-SLIP technique and shows a line A61 (solid line) that represents relation between the region R of the subject 13 and the longitudinal magnetization component Mz of the arterial blood AR at time t6. In the graph of FIG. 19B, a dash-dot-line indicates a line A5 1' in FIG. 18B.

As described with reference to FIG. 11, the line A6 represents the longitudinal magnetization component Mz of the arterial blood AR at time t6 according to the embodiment (FIG. 19A). In FIG. 19A, the longitudinal magnetization component Mz is set to −1 between the positions P4 and P6 at time t5'. The longitudinal magnetization component Mz is set to 0 between the positions P2 and P4. Since the arterial blood AR with the longitudinal magnetization component Mz set to 0 at time 5' flows by relaxing longitudinally, the longitudinal magnetization component Mz in the imaging region FOV becomes α (0.5 through 0.6) at time 6.

According to the Time-SLIP technique, however, the longitudinal magnetization component Mz in the upstream region UP is set to 1 at time t5' (see FIG. 18B). When the arterial blood AR with the longitudinal magnetization component Mz set to 1 in the upstream region UP flows into the imaging region FOV, the longitudinal magnetization component Mz between the positions P2 and P4 in the imaging region FOV is set to 1 at time t6.

According to the Time-SLIP technique, the longitudinal magnetization component Mz of in the imaging region FOV is set to −1 at time t5'. The longitudinal magnetization component Mz set to −1 at t5' for the arterial blood AR just recovers to 0 at time t6. The longitudinal magnetization component Mz between the positions P4 and P6 in the imaging region FOV becomes 0 at time t6. Accordingly, it is impossible to visually check the blood flow state of the artery between the positions P4 and P6 in the imaging region FOV.

As shown in FIG. 19A, the embodiment provides the longitudinal magnetization component Mz of the arterial blood AR with the value α (0.5 through 0.6) larger than zero throughout the entire imaging region FOV. Accordingly, the embodiment can image an arterial blood flow in the imaging region FOV more widely than the Time-SLIP technique for a distance x (between the positions P4 and P6).

The arterial blood AR flows into the imaging region FOV in the directions of not only SI (up and down) but also RL (left and right) and AP (forward and backward). The use of the embodiment can image the arterial blood AR more widely than the Time-SLIP technique for the distance x in the SI, RL, and AP directions. For example, the embodiment can sufficiently image the arterial blood AR in the kidney while the Time-SLIP technique cannot.

According to the embodiment (line A6), the longitudinal magnetization component Mz is set to α (0.5 through 0.6) in the imaging region FOV. Because of α<1, it might be supposed that the arterial blood AR according to the embodiment is less visible than that imaged according to the Time-SLIP technique in the range between the positions P2 and P4 of the imaging region FOV. According to the embodiment, however, the longitudinal magnetization component Mz of the arterial blood AR is sized to be α (0.5 through 0.6). In addition, the longitudinal magnetization component Mz of the venous blood VE is zero (see FIG. 11B). Therefore, the venous blood VE is actually not rendered in a blood flow image. Accordingly, it is expected that the blood flow state of the artery can be fully visible.

The longitudinal magnetization component Mz of the arterial blood AR is set to α when data acquisition starts according to the embodiment (see FIGS. 11A and 19A). A value greater than α can be assigned to the longitudinal magnetization component Mz of the arterial blood AR when data acquisition starts. For example, shortening the second wait time Tw2 can assign a value greater than α to the longitudinal magnetization component Mz of the arterial blood AR when data acquisition starts. The following describes why shortening the second wait time Tw2 can assign a value greater than α to the longitudinal magnetization component Mz of the arterial blood AR when data acquisition starts.

Let us consider two second wait times Tw2. One is the wait time Tw2=840 ms similarly to the embodiment. The other wait time Tw2 is shorter than 840 ms. The wait time Tw2 shorter than 840 ms is assumed to be 600 ms.

FIGS. 20 through 22 are graphs showing changes in the longitudinal magnetization component Mz of the arterial blood AR at time points of the pulse sequence 50 in FIG. 3 during the two wait times Tw2 (840 ms and 600 ms). The longitudinal magnetization component Mz of the arterial blood AR at times t1, t2, and t3 is the same as that depicted by the graphs of FIGS. 13, 14, and 15 independently of the values of the wait times Tw2 and a description is omitted.

When the wait times Tw2 are set to 840 ms and 600 ms, the graph in FIGS. 20A and 20B show the longitudinal magnetization component of the arterial blood AR at time t4.

FIGS. 20A and 20B show the longitudinal magnetization component Mz of the arterial blood AR at time t4 when the wait times Tw2 are set to 840 ms and 600 ms.

FIGS. 20A and 20B show lines A4 and A42. The line A4 shows relation between the region R of the subject 13 and the longitudinal magnetization component Mz of the arterial blood AR at time t4 when the wait time Tw2 is set to 840 ms. The line A42 shows relation between the region R of the subject 13 and the longitudinal magnetization component Mz of the arterial blood AR at time t4 when the wait time Tw2 is set to 600 ms.

The line A4 (wait time Tw2 set to 840 ms) shows that the longitudinal magnetization component Mz reaches the null point in the range to the left of the position Pa'. Since the wait time Tw2 is set to 600 ms on the line A42, the longitudinal magnetization component Mz on the line A42 does not reach the null point. On the line A42, Mz is set to $β(0<β<1)$ in the range to the left of the position Pa.

The third inversion period IR3 is provided immediately after time t4 (see FIG. 3). The nonselective RF inversion pulse P3 is applied during the third inversion period IR3. When the nonselective RF inversion pulse P3 is applied, the longitudinal magnetization component Mz of the arterial blood AR changes as shown in FIGS. 21A and 21B.

FIGS. 21A and 21B show the longitudinal magnetization component Mz of the arterial blood AR immediately after the third inversion period IR3 (time t5 in FIG. 3).

FIGS. 21A and 21B show lines A5 and A52. The line A5 represents the longitudinal magnetization component Mz of the arterial blood AR at time t5 when the wait time Tw2 is set to 840 ms. The line A52 represents the longitudinal magnetization component Mz of the arterial blood AR at time t5 when the wait time Tw2 is set to 600 ms.

Applying the nonselective inversion pulse P2 inverts the longitudinal magnetization component Mz of the arterial blood AR. As a result, the wait time Tw2 (=840 ms) causes the longitudinal magnetization component Mz to remain zero in the range to the left of the position Pa'. The wait time Tw2 (=600 ms) inverts the longitudinal magnetization component Mz to +β from −β in the range to the left of the position Pa.

The third inversion period IR3 is followed by the data acquisition period ACQ. The third wait time Tw3 is provided between the third inversion period IR3 and the data acquisition period ACQ. Similarly to the above-mentioned embodiment, the third wait time Tw3 is assumed to be 840 ms. The longitudinal magnetization component Mz of the arterial blood AR changes as shown in graphs of FIGS. 22A and 22B during the third wait time Tw3.

FIGS. 22A and 22B show the longitudinal magnetization component Mz of the arterial blood AR at the start time of the data acquisition period ACQ (time 6 in FIG. 3).

FIGS. 22A and 22B show lines A6 and A62. The line A6 represents the longitudinal magnetization component Mz of the arterial blood AR at time t6 when the wait time Tw2 is set to 840 ms. The line A52 represents the longitudinal magnetization component Mz of the arterial blood AR at time t6 when the wait time Tw2 is set to 600 ms.

The arterial blood AR relaxes longitudinally between times t5 and t6. When the wait time Tw2 is set to 840 ms, the longitudinal magnetization component Mz recovers to $\alpha$. When the wait time Tw2 is set to 600 ms, the longitudinal magnetization component Mz recovers to $\gamma$. In FIG. 21, the longitudinal magnetization component Mz with the wait time Tw2 set to 840 ms reaches the null point in the range to the left of the position Pa'. The longitudinal magnetization component Mz with the wait time Tw2 set to 600 ms indicates a value $\beta$ greater than the null point in the range to the left of the position Pa. As shown in FIGS. 22, the longitudinal magnetization component Mz with the wait time Tw2 set to 600 ms becomes greater than $\alpha$ and relaxes longitudinally up to $\gamma$.

Accordingly, shortening the wait time Tw2 can increase the longitudinal magnetization component Mz of the arterial blood AR at the time of starting the data acquisition.

As shown in FIG. 22B, however, shortening the wait time Tw2 zeros the longitudinal magnetization component Mz of the arterial blood AR in part of the imaging region FOV. Shortening the wait time Tw2 narrows the range of the arterial blood AR rendered in the imaging region FOV. It is preferable not to excessively shorten the wait time Tw2 when the arterial blood AR needs to be rendered in a wide range. The wait time Tw2 can be longer than the time period (840 ms) during which the longitudinal magnetization component Mz of the arterial blood AR reaches the null point from −1.

According to the embodiment, the third wait time Tw3 is configured to be equivalent to the time during which the longitudinal magnetization component Mz of the venous blood VE reaches the null point from −1. When the arterial blood AR can be sufficiently separated from the venous blood VE, the third wait time Tw3 can be longer or shorter than the time during which the longitudinal magnetization component Mz of the venous blood VE reaches the null point from −1.

To prevent the venous blood VE from being imaged, the embodiment configures the third wait time Tw3 to be equivalent to the time during with the longitudinal magnetization component Mz of the venous blood VE reaches the null point from −1. To prevent a tissue (e.g., the kidney 17) other than the venous blood VE from being imaged, the third wait time Tw3 just needs to be configured to a time during which the longitudinal magnetization component Mz of the other tissue reaches the null point from −1.

The embodiment images the arterial blood AR. Further, the invention can also image the venous blood VE. To image the venous blood VE, the third wait time Tw3 just needs to be configured to a time during which the longitudinal magnetization component Mz of the arterial blood AR or the other tissue (e.g., a motionless tissue) reaches the null point from −1.

The embodiment transmits the nonselective RF inversion pulses P1 and P3 during the first and third inversion periods IR1 and IR3. When the arterial blood AR flowing in the imaging region FOV can be sufficiently rendered, the selective RF inversion pulse may be transmitted instead of the nonselective RF inversion pulses P1 and P3.

According to the embodiment, the wait time Tw1 is several milliseconds but can be elongated. For example, the wait time Tw1 can be longer than the wait time Tw2. However, the short wait time Tw1 is preferable because elongating the wait time Tw1 causes the longitudinal magnetization component Mz=$\alpha$ of the arterial blood AR to approximate to zero.

While the embodiment images parts including the kidney 14, the invention can be applied to imaging of the other parts such as a head.

The embodiment acquires data about the arterial blood AR when a positive value is set to the longitudinal magnetization component Mz of the arterial blood AR. When the arterial blood AR can be emphasized more sufficiently than a background tissue, data about the arterial blood AR can be acquired even though a negative value is set to the longitudinal magnetization component Mz of the arterial blood AR.

Many widely different embodiments of the invention may be configured without departing from the spirit and the scope of the present invention. It should be understood that the present invention is not limited to the specific embodiments described in the specification, except as defined in the appended claim.

What is claimed is:

1. An MRI apparatus configured to image a subject such that arterial blood flowing from an upstream region to a downstream region through an imaging region of the subject is emphasized in image data over venous blood flowing in an opposing direction through the imaging region, said MRI apparatus comprising:
   a static magnetic field generating device configured to generate a static magnetic field to the subject in order to assign positive values to each of a longitudinal magnetization component of the arterial blood and a longitudinal magnetization component of the venous blood;
   a transmission coil configured to transmit an RF pulse to the subject;
   a first transmission coil control device configured to cause said transmission coil to transmit a first inversion pulse for inverting the longitudinal magnetization component of each of the arterial blood and the venous blood to negative values from the positive values;
   a second transmission coil control device configured to cause said transmission coil to transmit a second inversion pulse for inverting the longitudinal magnetization component of the venous blood to the positive value from the negative value inverted by the first inversion pulse;
   a third transmission coil control device configured to cause said transmission coil to transmit a third inversion pulse for inverting the longitudinal magnetization component of the venous blood to the negative value from the positive value inverted by the second inversion pulse;
   a fourth transmission coil control device configured to cause said transmission coil to transmit an excitation pulse for acquiring said image data from said imaging region;
   a first inversion pulse transmission control device configured to control the transmission of the second inversion pulse at a time point when a first wait time has elapsed after transmitting the first inversion pulse;
   a second inversion pulse transmission control device configured to control the transmission of the third inversion pulse at a time point when a second wait time has elapsed after transmitting the second inversion pulse; and
   a third inversion pulse transmission control device configured to control the transmission of the excitation pulse at a time point when a third wait time has elapsed after transmitting the third inversion pulse, wherein said third inversion pulse transmission control device is configured to determine the third wait time such that the excitation pulse is transmitted while an absolute value of the longitudinal magnetization component of the arterial blood is greater than an absolute value of the longitudinal magnetization component of the venous blood; wherein the second inversion pulse is a selective RF inversion pulse that selects the imaging region and the downstream region.

2. The MRI apparatus according to claim 1, wherein a total of the first and second wait times is equivalent to a time until the longitudinal magnetization component of the arterial blood reaches a null point, the longitudinal magnetization component having the negative value inverted by the first inversion pulse.

3. The MRI apparatus according to claim 1, wherein a total of the first and second wait times is shorter than a time until the longitudinal magnetization component of the arterial blood reaches a null point, the longitudinal magnetization component having the negative value inverted by the first inversion pulse.

4. The MRI apparatus according to claim 1, wherein the first wait time is shorter than the second wait time.

5. The MRI apparatus according to claim 1, wherein the third wait time is configured for a longitudinal magnetization component of the venous blood to reach a null point, the longitudinal magnetization component having the negative value inverted by the third inversion pulse.

6. The MRI apparatus according to claim 1, wherein the third inversion pulse inverts a longitudinal magnetization component of the arterial blood flowing into the imaging region.

7. The MRI apparatus according to claim 1, further comprising a gradient coil.

8. The MRI apparatus according to claim 1, further comprising a gradient coil control device configured to control a gradient coil such that said gradient coil applies a gradient pulse.

9. The MRI apparatus according to claim 1, further comprising an aspiration detection device configured to detect aspiration of the subject and to output an aspiration signal.

10. The MRI apparatus according to claim 9, further comprising a timing computation device configured to compute a timing to apply said first, second, and third inversion pulses and said excitation pulse based on the aspiration signal output from said aspiration detection device.

11. The MRI apparatus according to any one of claim 1, further comprising a heartbeat detection device configured to detect a heartbeat of the subject and to output an electrocardiographic signal.

12. The MRI apparatus according to claim 11, further comprising a timing computation device configured to compute a timing to apply said first, second, and third inversion pulses and said excitation pulse based on the electrocardiographic signal output from said heartbeat detection device.

13. The MRI apparatus according to claim 1, wherein the first inversion pulse is a nonselective RF inversion pulse.

14. The MRI apparatus according to claim 1, wherein the third inversion pulse is a nonselective RF inversion pulse.

15. A program stored on a non-transitory, tangible computer readable storage medium for an MRI apparatus configured to image a subject such that arterial blood flowing from an upstream region to a downstream region through an imaging region of the subject is emphasized in image data over venous blood flowing in an opposing direction through the imaging region, the MRI apparatus including a static magnetic field generating device configured to generate a static magnetic field to the subject in order to assign positive values to each of a longitudinal magnetization component of the arterial blood and a longitudinal magnetization component of the venous blood, and a transmission coil configured to transmit an RF pulse to the subject, said program configuring the MRI apparatus to function as:

a first transmission coil control device configured to cause the transmission coil to transmit a first inversion pulse for inverting the longitudinal magnetization component of each of the arterial blood and the venous blood to negative values from the positive values;

a second transmission coil control device configured to cause the transmission coil to transmit a second inversion pulse for inverting the longitudinal magnetization component of the venous blood to the positive value from the negative value inverted by the first inversion pulse;

a third transmission coil control device configured to cause the transmission coil to transmit a third inversion pulse for inverting the longitudinal magnetization component of the venous blood to the negative value from the positive value inverted by the second inversion pulse;

a fourth transmission coil control device configured to cause the transmission coil to transmit an excitation pulse for acquiring the image data from said imaging region;

a first inversion pulse transmission control device configured to control the transmission of the second inversion pulse at a time when a first wait time has elapsed after transmitting the first inversion pulse;

a second inversion pulse transmission control device configured to control the transmission of the third inversion pulse at a time point when a second wait time has elapsed after transmitting the second inversion pulse; and a third inversion pulse transmission control device configured to control the transmission of the excitation pulse at a time point when a third wait time has elapsed after transmitting the third inversion pulse, wherein the third inversion pulse transmission control device is configured to determine the third wait time such that the excitation pulse is transmitted while an absolute value of the longitudinal magnetization component of the arterial blood is greater than an absolute value of the longitudinal magnetization component of the venous blood; wherein the second inversion pulse is a selective RF inversion pulse that selects the imaging region and the downstream region.

16. The MRI apparatus according to claim 1, wherein the first inversion pulse is a nonselective RF inversion pulse and the third inversion pulse is a nonselective RF inversion pulse.

* * * * *